US012150899B2

(12) United States Patent
Simoneau et al.

(10) Patent No.: US 12,150,899 B2
(45) Date of Patent: Nov. 26, 2024

(54) AUTOMATED CALIBRATION OF LASER SYSTEM AND TOMOGRAPHY SYSTEM WITH FLUORESCENT IMAGING OF SCAN PATTERN

(71) Applicant: AMO Development, LLC, Irvine, CA (US)

(72) Inventors: Michael Simoneau, Morgan Hall, CA (US); John Scot Hart, Menlo Park, CA (US); Georg Schuele, Portola Valley, CA (US)

(73) Assignee: AMO Development, LLC, Irvine, CA (US)

( * ) Notice: Subject to any disclaimer, the term of this patent is extended or adjusted under 35 U.S.C. 154(b) by 0 days.

(21) Appl. No.: 18/324,733

(22) Filed: May 26, 2023

(65) Prior Publication Data

US 2023/0293349 A1    Sep. 21, 2023

Related U.S. Application Data

(60) Continuation of application No. 17/331,589, filed on May 26, 2021, now Pat. No. 11,660,230, which is a continuation of application No. 16/166,661, filed on Oct. 22, 2018, now Pat. No. 11,020,273, which is a
(Continued)

(51) Int. Cl.
*A61F 9/008* (2006.01)
*A61B 90/00* (2016.01)
*B23K 26/082* (2014.01)

(52) U.S. Cl.
CPC ........ *A61F 9/00814* (2013.01); *A61B 90/361* (2016.02); *A61F 9/008* (2013.01); *A61F 9/00823* (2013.01); *A61F 9/0084* (2013.01); *A61F 2009/00846* (2013.01); *A61F 2009/00851* (2013.01); *A61F 2009/00855* (2013.01);
(Continued)

(58) Field of Classification Search
CPC ..... A61F 9/00814; A61F 9/008; A61B 90/361
See application file for complete search history.

(56) References Cited

U.S. PATENT DOCUMENTS

| 5,720,894 A | 2/1998 | Neev et al. |
| 5,928,221 A | 7/1999 | Sasnett et al. |
| 5,957,915 A | 9/1999 | Trost |

(Continued)

FOREIGN PATENT DOCUMENTS

WO    2014158615 A1    10/2014

*Primary Examiner* — Hugh Maupin

(57) ABSTRACT

A laser system calibration method and system are provided. In some methods, a calibration plate may be used to calibrate a video camera of the laser system. The video camera pixel locations may be mapped to the physical space. A xy-scan device of the laser system may be calibrated by defining control parameters for actuating components of the xy-scan device to scan a beam to a series of locations. Optionally, the beam may be scanned to a series of locations on a fluorescent plate. The video camera may be used to capture reflected light from the fluorescent plate. The xy-scan device may then be calibrated by mapping the xy-scan device control parameters to physical locations. A desired z-depth focus may be determined by defining control parameters for focusing a beam to different depths. The video camera or a confocal detector may be used to detect the scanned depths.

8 Claims, 18 Drawing Sheets

Related U.S. Application Data division of application No. 14/666,743, filed on Mar. 24, 2015, now Pat. No. 10,105,261.

(60) Provisional application No. 61/969,688, filed on Mar. 24, 2014.

(52) U.S. Cl.
CPC ............... *A61F 2009/00857* (2013.01); *A61F 2009/00897* (2013.01); *B23K 26/082* (2015.10)

(56) References Cited

U.S. PATENT DOCUMENTS

| | | |
|---|---|---|
| 5,984,916 A | 11/1999 | Lai |
| 6,019,472 A | 2/2000 | Koester et al. |
| 6,454,761 B1 | 9/2002 | Freedman |
| 7,655,002 B2 | 2/2010 | Myers, I et al. |
| 7,717,907 B2 | 5/2010 | Ruiz et al. |
| 8,262,646 B2 | 9/2012 | Frey et al. |
| 8,350,183 B2 | 1/2013 | Vogel et al. |
| 8,382,745 B2 | 2/2013 | Naranjo-Tackman et al. |
| 8,414,564 B2 | 4/2013 | Goldshleger et al. |
| 10,105,261 B2 | 10/2018 | Simoneau et al. |
| 11,020,273 B2 | 6/2021 | Simoneau et al. |
| 11,660,230 B2 | 5/2023 | Simoneau et al. |
| 2004/0147910 A1* | 7/2004 | Fujieda ............... A61F 9/00814 606/5 |
| 2005/0205778 A1 | 9/2005 | Kitai et al. |
| 2006/0103839 A1 | 5/2006 | Somani et al. |
| 2007/0173792 A1 | 7/2007 | Arnoldussen |
| 2007/0225692 A1 | 9/2007 | Somani et al. |
| 2011/0172649 A1 | 7/2011 | Schuele et al. |
| 2011/0202046 A1 | 8/2011 | Angeley et al. |
| 2011/0267446 A1 | 11/2011 | Chernyak et al. |
| 2011/0275932 A1 | 11/2011 | Leblond et al. |
| 2011/0319873 A1* | 12/2011 | Raksi ...................... A61F 9/009 606/1 |
| 2011/0319875 A1 | 12/2011 | Loesel et al. |
| 2014/0058367 A1 | 2/2014 | Dantus |
| 2014/0128821 A1* | 5/2014 | Gooding ................. A61F 9/009 606/4 |
| 2014/0128853 A1 | 5/2014 | Angeley et al. |
| 2014/0163534 A1 | 6/2014 | Angeley et al. |
| 2014/0316389 A1 | 10/2014 | Schuele et al. |
| 2015/0083902 A1 | 3/2015 | Akselrod et al. |
| 2015/0141972 A1* | 5/2015 | Woodley ............ G01B 9/02091 606/5 |

\* cited by examiner using the second support assembly to support a second reflector configured to reflect the electromagnetic radiation beam to propagate along a portion of the variable optical path so as to be incident on the first reflector - 222 using the sensor to generate the intensity signal comprises passing a reflected portion of the electromagnetic radiation beam through an aperture to block portions of the electromagnetic radiation beam reflected from locations other than the focal point location - 224

*FIG. 5* passing the electromagnetic radiation beam through a polarization-sensitive device - 226 modifying polarization of at least one of the electromagnetic radiation beam and a portion of the electromagnetic radiation beam reflected from the focal point location - 228 using the polarization-sensitive device to reflect a portion of the electromagnetic radiation beam reflected from the focal point location so as to be incident upon the sensor - 230

*FIG. 6*

```
Low Resolution
VIDEO LUT              Total # of points: 9025
              Given:  X, Y, Z, CL         Find: Pixel X, Pixel Y
232 →         X,Y:  Range: -9 to 9mm      Pixel X, Pixel Y: -543 to 543 plx
                    Step: 1mm
              Z:    Range: 6 to 10mm
                    Step: 1mm
              CL:   Range: -1 to 1mm
                    Step: 0.5mm
```
(230, 234)
FIG. 18
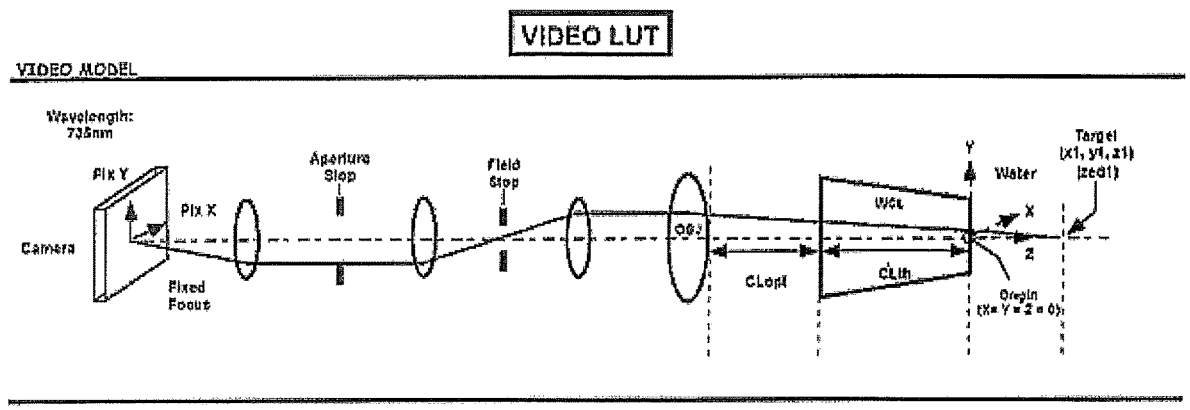
FIG. 19
FIG. 20

| OF LUT, | | Xm(UF) [OPTDOG], Xm(UF) [OPTDOG], ZL (UF) ]mm] @1031nm GIVEN X[mm], Y[mm], Z[mm] CLopt[mm], CLth[mm] | | | | | | | | | | | | |
|---|---|---|---|---|---|---|---|---|---|---|---|---|---|---|
| BASE CASES | NA | OSLO(ZL) | OPL(UF) | X | Y | Z | CLopt | CLth | XM(UF) | YM(UF) | ZL(UF) | ZED [UF] | DZ | STROHL |
| 1-ORIGIN | 0.115 | 31.9856, | 1803.1556, | 0.000, | -0.003, | 0.000, | 21.720, | 12.000, | 0.0000, | 0.0000, | 4.3104, | 0.0002, | 0.000, | 0.827 |
| 2-ORIGIN | 0.125 | 29.3254, | 1808.7800, | 0.000, | -0.002, | 6.000, | 21.720, | 12.000, | 0.0000, | 0.0000, | 6.9806, | 3.3124, | 0.000, | 0.971 |
| 3-LIMBOS X | 0.138, | 27.1908, | 1813.6048, | 6.000, | -0.000, | 8.000, | 21.720, | 12.000, | 6.8589, | 0.0000, | 9.1055, | 5.2248, | -0.000, | 0.619 |
| 4-LIMBOS Y | 0.138, | 27.1980, | 1813.7198, | 0.000, | 6.000, | 8.000, | 21.720, | 12.000, | 0.0000, | 5.9588, | 9.0980, | 5.2823, | 0.000, | 0.690 |

UF LUT: (AT LOW LOW RESOLUTION (3.5mm INCREMENTS XY, 3mm IN Z, 1um IN CLopt, 150mm IN CLth); 900 ENTRIES)

| Xmin | Xinc | Xmax | Ymin | Yinc | Ymax | Zmin | Zinc | CLth | Zmax | CLoptmin | CLoptinc | CLoptmax | CLthmin | CLthinc | CLthmax |
|---|---|---|---|---|---|---|---|---|---|---|---|---|---|---|---|
| -7.00, | 3.3, | 7.00, | -7.00, | 3.5, | 7.00, | 5.00, | 3.0, | 11.850, | 14.00, | 20.72, | 1.0, | 22.72, | 11.85, | 0.15, | 12.15 |
| STEP | OSLO(IL) | OPL(-) | X | Y | Z | CLopt | CLth | Xm(UF) | Ym(UF) | ZL(UF) | ZED(-) | Dz | STROHL | FLAG |
| 1, | 29.7342, | 1, | -7.000, | -7.000, | 5.000, | 20.72, | 11.850, | -6.7679, | -7.0116, | 6.5618, | 1, | 0.0020, | 0.01, | 1 |
| 2, | 29.8844, | 1, | -3.500, | -7.000, | 5.000, | 20.72, | 11.850, | -3.3682, | -6.9626, | 6.4116, | 1, | 0.0041, | 0.07, | 1 |
| 3, | 29.9327, | 1, | 0.000, | -7.000, | 5.000, | 20.72, | 11.850, | 0.0000, | -6.9466, | 6.3633, | 1, | 0.0011, | 0.20, | 1 |
| 4, | 29.8844, | 1, | 3.500, | -7.000, | 5.000, | 20.72, | 11.850, | 3.3682, | -6.9626, | 6.4116, | 1, | 0.0014, | 0.07, | 1 |
| 5, | 29.7337, | 1, | 7.000, | -7.000, | 5.000, | 20.72, | 11.850, | 6.7679, | -7.0116, | 6.5623, | 1, | 0.0028, | 0.01, | 1 |
| 6, | 29.8861, | 1, | -7.000, | -3.500, | 5.000, | 20.72, | 11.850, | -6.7045, | -3.4897, | 6.4089, | 1, | 0.0008, | 0.15, | 1 |
| 7, | 30.0310, | 1, | -3.500, | -3.500, | 5.000, | 20.72, | 11.850, | -3.3372, | -3.4652, | 6.2650, | 1, | 0.0003, | 0.59, | 1 |
| 8, | 30.0775, | 1, | 0.000, | -3.500, | 5.000, | 20.72, | 11.850, | 0.0000, | -3.4572, | 6.2185, | 1, | 0.0003, | 0.74, | 1 |
| 9, | 30.0310, | 1, | 3.500, | -3.500, | 5.000, | 20.72, | 11.850, | 3.3372, | -3.4652, | 6.2650, | 1, | 0.0002, | 0.59, | 1 |
| 10, | 29.8862, | 1, | 7.000, | -3.500, | 5.000, | 20.72, | 11.850, | 6.7045, | -3.4897, | 6.4098, | 1, | 0.0007, | 0.15, | 1 |
| 11, | 29.9340, | 1, | -7.000, | -0.000, | 5.000, | 20.72, | 11.850, | -6.6828, | 0.0000, | 6.3620, | 1, | 0.0001, | 0.53, | 1 |
| 12, | 30.0769, | 1, | -3.500, | -0.002, | 5.000, | 20.72, | 11.850, | -3.3266, | 0.0000, | 6.2191, | 1, | -0.0000, | 0.97, | 1 |
| 13, | 30.1229, | 1, | -0.000, | -0.002, | 5.000, | 20.72, | 11.850, | 0.0000, | 0.0000, | 6.1731, | 1, | -0.0002, | 0.95, | 1 |
| 14, | 30.0770, | 1, | 3.500, | -0.002, | 5.000, | 20.72, | 11.850, | 3.3266, | 0.0000, | 6.2190, | 1, | -0.0002, | 0.97, | 1 |
| 15, | 29.9340, | 1, | 7.000, | -0.002, | 5.000, | 20.72, | 11.850, | 6.6828, | 0.0000, | 6.3620, | 1, | 0.0000, | 0.53, | 1 |
| 16, | 29.8812, | 1, | -7.000, | 3.500, | 5.000, | 20.72, | 11.850, | -6.7014, | 3.4874, | 6.4148, | 1, | 0.0005, | 0.17, | 1 |
| 17, | 30.0259, | 1, | -3.500, | 3.500, | 5.000, | 20.72, | 11.850, | -3.3357, | 3.4652, | 6.2701, | 1, | 0.0002, | 0.64, | 1 |
| 18, | 30.0724, | 1, | 0.000, | 3.500, | 5.000, | 20.72, | 11.850, | 0.0000, | 3.4579, | 6.2236, | 1, | 0.0001, | 0.79, | 1 |
| 19, | 30.0259, | 1, | 3.500, | 3.500, | 5.000, | 20.72, | 11.850, | -3.3357, | 3.4652, | 6.2701, | 1, | 0.0002, | 0.64, | 1 |
| 20, | 29.8812, | 1, | -7.000, | 3.500, | 5.000, | 20.72, | 11.850, | -6.7014, | 3.4874, | 6.4248, | 1, | 0.0005, | 0.17, | 1 |

15 COLUMNS

FIG. 21

AUTOMATED CALIBRATION OF LASER SYSTEM AND TOMOGRAPHY SYSTEM WITH FLUORESCENT IMAGING OF SCAN PATTERN

CROSS-REFERENCES TO RELATED APPLICATIONS

This application is a continuation and claims priority to U.S. patent application Ser. No. 17/331,589, filed May 26, 2021, allowed, which is a continuation and claims priority to U.S. patent application Ser. No. 16/166,661, filed Oct. 22, 2018, now U.S. Pat. No. 11,020,273, issued Jun. 1, 2021, which is a divisional and claims priority to U.S. patent application Ser. No. 14/666,743, filed Mar. 24, 2015, now U.S. Pat. No. 10,105,261, issued Oct. 23, 2018, which claims priority to U.S. Provisional Application No. 61/969,688 filed on Mar. 24, 2014. The entire contents of the above-referenced applications are incorporated herein by reference.

BACKGROUND

Over the years, surgical laser systems have replaced manual surgical tools in ophthalmic procedures. Indeed, with applications in a variety of different procedures, surgical laser systems have become ubiquitous in eye surgery.

For instance, in the well-known procedure known as LASIK (laser-assisted in situ keratomileusis), a laser eye surgery system employing ultraviolet radiation is used for ablating and reshaping the anterior surface of the cornea to correct a refractive condition, such as myopia or hyperopia. Prior to ablation during LASIK, the cornea is incised with another surgical laser system employing a non-ultraviolet, ultra-short pulsed laser beam to create a flap to expose an underlying portion of the corneal bed so it can be then be ablated and reshaped with ultraviolet laser beams. Afterwards, the treated portion is covered with the flap.

Laser eye surgery systems have also been developed for cataract procedures. These systems can be used for various surgical procedures, including for instance: (1) creating one or more incisions in the cornea or in the limbus to reshape the cornea, (2) creating one or more incisions in the cornea to provide access for a cataract surgery instrument and/or to provide access for implantation of an intraocular lens, (3) incising the anterior lens capsule (anterior capsulotomy) to provide access for removing a cataractous lens, (4) segmenting and/or fragmenting a cataractous lens, and/or (5) incising the posterior lens capsule (posterior capsulotomy) for various cataract-related procedures.

Often, calibrating various laser surgical systems can be cumbersome, time-consuming, and more complex than desired. For example, in some situations, the calibration may require manual calibration of the scanning systems with a calibration plate, which can be time-intensive. Thus, providing laser eye surgery systems with improved characteristics for system calibration and related methods would be beneficial.

SUMMARY

Accordingly, this disclosure provides laser calibration systems and related methods that substantially obviate one or more problems due to limitations and disadvantages of the related art. As mentioned earlier, laser system calibration can be time-intensive, at times requiring manual calibration of scanning systems with a calibration plate. As such, providing systems and methods for automatically calibrating a laser system would be beneficial.

Thus, in some embodiments, a method of calibrating a laser system with a treatment space is provided. The laser system may include a scanning system and a camera. The camera may comprise a sensor with sensor surface locations. In some embodiments, the sensor may comprise an array of pixels and the sensor surface locations may be pixel locations. Some embodiments provide a mapping of sensor surface locations to a treatment space of the laser system is provided. In some embodiments, the method may include a step of mapping camera pixel locations to the treatment space. Using the scanning system, the laser system's electromagnetic radiation beam may be scanned to a series of scanning locations of a fluorescent material. The series of locations may be scanned by moving the electromagnetic beam orthogonally relative to a propagation direction of the beam. The camera may capture light that is emitted from the series of locations of the fluorescent material in response to the scanned electromagnetic radiation beam. Thereafter, the scanning system may be calibrated with the treatment space based on the series of locations captured by the video camera, and by mapping the sensor surface locations to the treatment space.

In some embodiments, the sensor surface locations may be mapped to the treatment space using polynomial fitting or lookup tables. The camera may be calibrated by using it to view a calibration plate positioned orthogonally relative to the camera at a known distance. The calibration plate may define discrete known locations in the treatment space. Distortions of the camera may be removed based on the locations defined by the calibration plate. In some embodiments, the calibration plate may be a calibration grid where grid intersections define discrete known locations in treatment space. Optionally, the calibration plate may include a plurality of through holes for passing electromagnetic radiation, and the plurality of through holes may define discrete known locations in treatment space.

In some embodiments, the scanning system includes an xy-scan device. The method may include a step of defining control parameters for the xy-scan device of the scanning system to scan the laser system's electromagnetic radiation beam to the series of scanning locations of the fluorescent material. Thereafter, the treatment space may be mapped to the control parameters of the xy-scan device. In some embodiments, the treatment space may be mapped to the control parameters of the xy-scan device with polynomial fit or with lookup tables. The treatment space may be mapped to the control parameters of the xy-scan device with the polynomial fit and the polynomial fit may be independent of a z-depth focus in some embodiments. Optionally, the control parameters of the xy-scan device may be defined so as to scan the electromagnetic radiation beam of the laser system to locations of a rectilinear grid or of a square lattice.

In some embodiments, the scanning system may include a z-scan device that is configured to vary a convergence depth of the electromagnetic radiation beam within the treatment space. The method may include the steps of calibrating the z-scan device of the scanning system by defining control parameters for the z-scan device for focusing the electromagnetic radiation beam to a series of depth locations. The camera or a confocal detector may be used to capture light emitted from the fluorescent plate at the series of depth locations in response to the electromagnetic radiation beam focusing. Thereafter, the treatment space may be mapped to the control parameters of the z-scan device. In some embodiments, a depth between the laser system and the fluorescent material may be varied using a jack supporting the fluorescent material. The jack may be configured to set the depth between the laser system and the fluorescent material. It may also be automated to vary height.

In further aspects of the invention, a laser system may be provided. The laser system may include an electromagnetic radiation beam source configured to output a beam along a path toward a treatment space. It may also include a scanning system that is configured to direct the outputted beam to a plurality of locations in the treatment space. The laser system may also include a camera for capturing images of the treatment space. A processor may be coupled with the scanning system and the camera. The processor may be configured to calibrate the scanning system by scanning the laser system's electromagnetic radiation beam to a series of scanning locations of a fluorescent material. The series of locations may be orthogonal relative to a propagation direction of the electromagnetic radiation beam. Using the camera, the processor may further capture light emitted from the series of locations of the fluorescent material in response to the scanned electromagnetic radiation beam. Thereafter, the processor may calibrate the scanning system with the treatment space based on the series of locations captured by the camera.

In some embodiments, the camera may include a sensor having an array of pixels and each pixel may have a pixel location. The processor may map camera pixel locations to the treatment space by using the camera to view a calibration plate positioned orthogonally relative to the camera at a known distance. The calibration plate may include a calibration grid or a plurality of through holes for passing electromagnetic radiation.

In some embodiments, the scanning system may include an xy-scan device. The processor may calibrate the scanning system by defining control parameters for the xy-scan device for scanning the electromagnetic radiation beam to the series of scanning locations of the fluorescent material. The processor may be used to map the treatment space to the control parameters of the xy-scan device with a polynomial fit, and the polynomial fit may be independent of a z-depth focus. In some embodiments, the processor may define the control parameters of the xy-scan device to scan the laser system's electromagnetic radiation beam to locations of a rectilinear grid or a square lattice.

In some embodiments, the scanning system may include a z-scan device that is configured to vary the electromagnetic radiation beam's convergence depth within the treatment space. The processor may calibrate the scanning system by defining control parameters for the z-scan device to focusing the electromagnetic radiation beam to a series of depth locations. The camera or a confocal detector may be used to capture light emitted from the fluorescent plate at the series of depth locations in response to focusing the electromagnetic radiation beam. The treatment space may then be mapped to the control parameters of the z-scan device. In some embodiments, the system may include a jack for supporting the fluorescent material. The jack may be configured to set the depth between the laser system and the fluorescent material.

In some aspects of the invention, a non-transitory computer readable storage medium comprising a set of computer executable instructions for calibrating a laser system with a treatment space is provided. Execution of the instructions by a computer processor may cause the processor to carry out the steps of mapping sensor surface locations to the treatment space. The processor may further send instructions to the scanning system to scan the laser system's electromagnetic radiation beam to a series of scanning locations of a fluorescent material. The series of locations may be orthogonal relative to a propagation direction of the electromagnetic radiation beam. The processor may also receive data on the camera's capture of light emitted from the series of locations of the fluorescent material in response to the scanned electromagnetic radiation beam. It may also calibrate the scanning system with the treatment space based on the series of locations captured by the camera, and on the camera pixel locations mapped to the treatment space.

In some embodiments, execution of the instructions by the computer processor may cause the processor to further carry out a step of calibrating the camera by receiving camera data of a calibration plate positioned orthogonally relative to the camera at a known distance. The calibration plate may define discrete known locations in the treatment space. Thereafter, the processor may remove out distortions of the camera based on the locations defined by the calibration plate.

In some embodiments, where the scanning system comprises an xy-scan device, the processor may calibrate the scanning system by defining control parameters for the xy-scan device to scan the laser system's electromagnetic radiation beam to the series of scanning locations of the fluorescent material. Thereafter, the treatment space may be mapped to the control parameters of the xy-scan device. In some embodiments, the processor may define the control parameters of the xy-scan device so as to scan the electromagnetic radiation beam to locations of a rectilinear grid or a square lattice. The scanning system may comprise a z-scan device that is configured to vary a convergence depth of the electromagnetic radiation beam within the treatment space. In that case, the processor may calibrate the scanning system by defining control parameters for the z-scan device for focusing the electromagnetic radiation beam to a series of depth locations. The processor may receive camera data or confocal detector data of light emitted from the fluorescent plate at the series of depth locations in response to focusing the electromagnetic beam. Thereafter, the treatment space may be mapped to the control parameters of the z-scan device.

In some embodiments, execution of the instructions by the computer processor may cause the processor to further carry out the step of varying a depth between the laser system and the fluorescent material by sending actuation instructions to a jack supporting the fluorescent material. The jack may be configured to set the depth between the laser system and the fluorescent material.

This summary and the following description are merely exemplary, illustrative, and explanatory, and are not intended to limit, but to provide further explanation of the invention as claimed. Additional features, aspects, objects and advantages of embodiments of this invention are set forth in the descriptions, drawings, and the claims, and in part, will be apparent from the drawings and detailed description, or may be learned by practice. The claims are incorporated by reference.

BRIEF DESCRIPTION OF THE DRAWINGS

The novel features of the invention are set forth with particularity in the appended claims. A better understanding of the features and advantages of the present invention will be obtained by referring to the following detailed description that sets forth illustrative embodiments using principles of the invention, as well as to the accompanying drawings of which:

FIGS. 4, 5, and 6 are simplified block diagrams of optional acts that can be accomplished in the method of FIG. 3 according to many embodiments.

FIG. 18 shows a look-up table summary for a video camera according to many embodiments.

FIG. 19 shows an optical schematic of the components corresponding to the look-up table of FIG. 18.

FIG. 20 shows the input and output of the look-up table as shown in FIGS. 18 and 19.

FIG. 21 shows structure and excerpt of the look-up table as shown in FIGS. 18 to 20.

DETAILED DESCRIPTION

The following description describes various embodiments of the present invention. For purposes of explanation, specific configurations and details are set forth so as to provide a thorough understanding of the embodiments. It will also, however, be apparent to one skilled in the art that embodiments of the present invention can be practiced without certain specific details. Further, to avoid obscuring the embodiment being described, various well-known features may be omitted or simplified in the description.

Systems for imaging and/or treating a patient's eye(s) are provided. In many embodiments, a free-floating mechanism provides a variable optical path by which a portion of an electromagnetic beam reflected from a focal point disposed within the eye is directed to a path length insensitive imaging assembly, such as a confocal detection assembly. In many embodiments, the free-floating mechanism is configured to accommodate movement of the patient while maintaining alignment between an electromagnetic radiation beam and the patient. The electromagnetic radiation beam can be configured for imaging the eye, for treating the eye, and for imaging as well as treating the eye.

Figure 1:
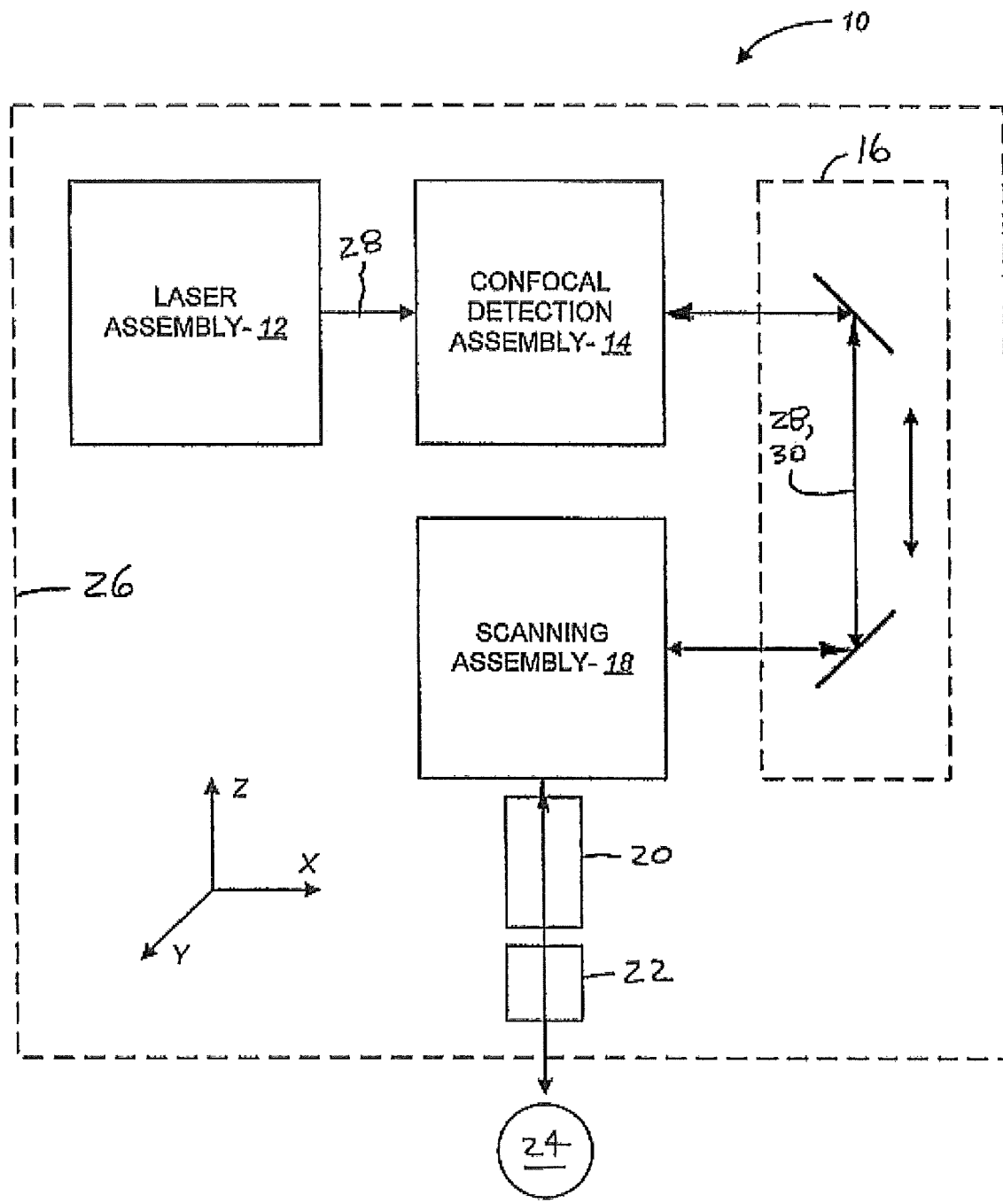
FIG. 1 is a schematic diagram of a laser surgery system according to many embodiments in which a patient interface device is coupled to a laser assembly and a detection assembly by way of a scanning assembly and a free-floating mechanism that supports the scanning assembly.

Referring now to the drawings in which like numbers refer to similar elements, FIG. 1 schematically illustrates a laser surgery system 10 according to many embodiments. The laser surgery system 10 may include a laser assembly 12, a confocal detection assembly 14, a free-floating mechanism 16, a scanning assembly 18, an objective lens assembly 20, and a patient interface device 22. The patient interface device 22 may be configured to interface with a patient 24. The patient interface device 22 may be supported by the objective lens assembly 20. The objective lens assembly 20 may be supported by the scanning assembly 18. The scanning assembly 18 may be supported by the free-floating mechanism 16. The free-floating mechanism 16 may have a portion having a fixed position and orientation relative to the laser assembly 12 and the confocal detection assembly 14.

In some embodiments, the patient interface device 22 may be configured to interface with an eye of the patient 24. For example, the patient interface device 22 can be configured to be coupled via vacuum suction to an eye of the patient 24 as described in co-pending U.S. patent application Ser. No. 14/068,994, entitled "Liquid Optical Interface for Laser Eye Surgery System," filed Oct. 31, 2013, the entire disclosure of which is incorporated herein by reference. The patient interface 22 may include an optically transmissive structure which may comprise an interface lens that is configured to be aligned with the system and an axis of eye. The patient interface lens can be placed on the patient's eye for surgery, and the optically transmissive structure can be placed at a distance from the objective lens. In many embodiments, the optically transmissive structure comprises a lens placed at a contact lens optical distance (hereinafter "CLopt"). The optically transmissive structure may comprise a thickness, which may comprise a thickness of the contact lens, for example. In many embodiments, although the optically transmissive structure comprising the contact lens may contact the eye, the contact lens may be separated from the cornea with a gap extending between the lens and the vertex of the cornea such that the posterior surface of the contact lens contacts a solution comprising saline or a viscoelastic solution.

The laser surgery system 10 can further optionally include a base assembly 26 that can be fixed in place or repositionable. For example, the base assembly 26 can be supported by a support linkage that is configured to allow selective repositioning of the base assembly 26 relative to a patient and secure the base assembly 26 in a selected fixed position relative to the patient. Such a support linkage can be supported in any suitable manner such as by a fixed support base or by a movable cart that can be repositioned to a suitable location adjacent to a patient. In many embodiments, the support linkage includes setup joints with each setup joint being configured to permit selective articulation of the setup joint and can be selectively locked to prevent inadvertent articulation of the setup joint, thereby securing the base assembly 26 in a selected fixed position relative to the patient when the setup joints are locked.

In many embodiments, the laser assembly 12 may be configured to emit an electromagnetic radiation beam 28. The beam 28 can include a series of laser pulses of any suitable energy level, duration, and repetition rate.

In many embodiments, the laser assembly 12 incorporates femtosecond (FS) laser technology. By using femtosecond laser technology, a short duration (e.g., approximately $10^{-13}$ to $10^{-15}$ seconds in duration) laser pulse (with energy level in the micro joule range) can be delivered to a tightly focused point to disrupt tissue, thereby substantially lowering the energy level required to image and/or modify an intraocular target as compared to laser pulses having longer durations.

The laser assembly 12 can produce laser pulses having a wavelength suitable to treat and/or image tissue. For example, the laser assembly 12 can be configured to emit an electromagnetic radiation beam 28 such as that emitted by any of the laser surgery systems described in co-pending U.S. patent application Ser. No. 14/069,044, entitled "Laser Eye Surgery System," filed Oct. 31, 2013; and U.S. patent application Ser. No. 12/987,069, entitled "Method and System For Modifying Eye Tissue and Intraocular Lenses," filed Jan. 7, 2011, the full disclosures of which are incorporated herein by reference. For example, the laser assembly 12 can produce laser pulses having a wavelength from 1020 nm to 1050 nm. For example, the laser assembly 12 can have a diode-pumped solid-state configuration with a 1030 (+/−5) nm center wavelength. As another example, the laser assembly 12 can produce laser pulses having a wavelength 320 nm to 430 nm. Further, the laser assembly 12 can include an Nd:YAG laser source operating at the 3rd harmonic wavelength (355 nm) and producing pulses having 50 pico second to 15 nano second pulse duration. Depending on the spot size, typical pulse energies used can be in the nano joule to micro joule range. The laser assembly 12 can also include two or more lasers of any suitable configuration.

The laser assembly 12 can include control and conditioning components. For example, such control components can include components such as a beam attenuator to control the energy of the laser pulse and the average power of the pulse train, a fixed aperture to control the cross-sectional spatial extent of the beam containing the laser pulses, one or more power monitors to monitor the flux and repetition rate of the beam train and therefore the energy of the laser pulses, and a shutter to allow/block transmission of the laser pulses. Such conditioning components can include an adjustable zoom assembly and a fixed optical relay to transfer the laser pulses over a distance while accommodating laser pulse beam positional and/or directional variability so as to provide increased tolerance for component variation.

In many embodiments, the laser assembly 12 and the confocal detection assembly 14 may have fixed positions relative to the base assembly 26. The beam 28 emitted by the laser assembly 12 may propagate along a fixed optical path through the confocal detection assembly 14 to the free-floating mechanism 16. The beam 28 may propagate through the free-floating mechanism 16 along a variable optical path 30, which may deliver the beam 28 to the scanning assembly 18. In many embodiments, the beam 28 emitted by the laser assembly 12 may be collimated so that the beam 28 is not impacted by patient movement induced changes in the length of the optical path between the laser assembly 12 and the scanner 16. The scanning assembly 18 may be operable to scan the beam 28 (e.g., via controlled variable deflection of the beam 28) in at least one dimension. In many embodiments, the scanning assembly 18 is operable to scan the beam 28 in two dimensions transverse to the direction of propagation of the beam 28 and may be further operable to scan the location of a focal point of the beam 28 in the direction of propagation of the beam 28. The scanned beam may be emitted from the scanning assembly 18 to propagate through the objective lens assembly 20, through the interface device 22, and to the eye of the patient 24.

The free-floating mechanism 16 may be configured to accommodate a range of movement of the patient 24 relative to the laser assembly 12 and the confocal detection assembly 14 in one or more directions while maintaining alignment of the beam 28 emitted by the scanning assembly 18 with the patient 24. For example, in many embodiments, the free-floating mechanism 16 may be configured to accommodate a range movement of the patient 24 in any direction defined by any combination of unit orthogonal directions (X, Y, and Z).

The free-floating mechanism 16 may support the scanning assembly 18 and may provide the variable optical path 30, which may change in response to movement of the patient 24. Because the patient interface device 22 may be interfaced with the patient 24, movement of the patient 24 may result in corresponding movement of the patient interface device 22, the objective lens assembly 20, and the scanning assembly 18. The free-floating mechanism 16 can include, for example, any suitable combination of a linkage that accommodates relative movement between the scanning assembly 18 and, for example, the confocal detection assembly 24, and optical components suitably tied to the linkage so as to form the variable optical path 30. Optionally, the free-floating mechanism 16 can be configured as described in U.S. patent application Ser. No. 14/191,095 and PCT Application No. PCT/US2014/018752, filed Feb. 26, 2014 and entitled "Laser Surgery System," the entire disclosure of which is incorporated herein by reference.

A portion of the electromagnetic radiation beam 28 may reflect from an eye tissue at the focal point and may propagate back to the confocal detection assembly 14. Specifically, a reflected portion of the electromagnetic radiation beam 28 may travel back through the patient interface device 22, back through the objective lens assembly 20, back through (and de-scanned by) the scanning assembly 18, back through the free-floating mechanism 16 (along the variable optical path 30), and to the confocal detection assembly 14. In many embodiments, the reflected portion of the electromagnetic radiation beam that travels back to the confocal detection assembly 14 may be directed to be incident upon a sensor that generates an intensity signal indicative of intensity of the incident portion of the electromagnetic radiation beam. The intensity signal, coupled with associated scanning of the focal point within the eye, can be processed in conjunction with the parameters of the scanning to, for example, image/locate structures of the eye, such as the anterior surface of the cornea, the posterior surface of the cornea, the iris, the anterior surface of the lens capsule, and the posterior surface of the lens capsule. In many embodiments, the amount of the reflected electromagnetic radiation beam that travels to the confocal detection assembly 14 may be substantially independent of expected variations in the length of the variable optical path 30 due to patient movement, thereby enabling the ability to ignore patient movements when processing the intensity signal to image/locate structures of the eye.

Figure 2:
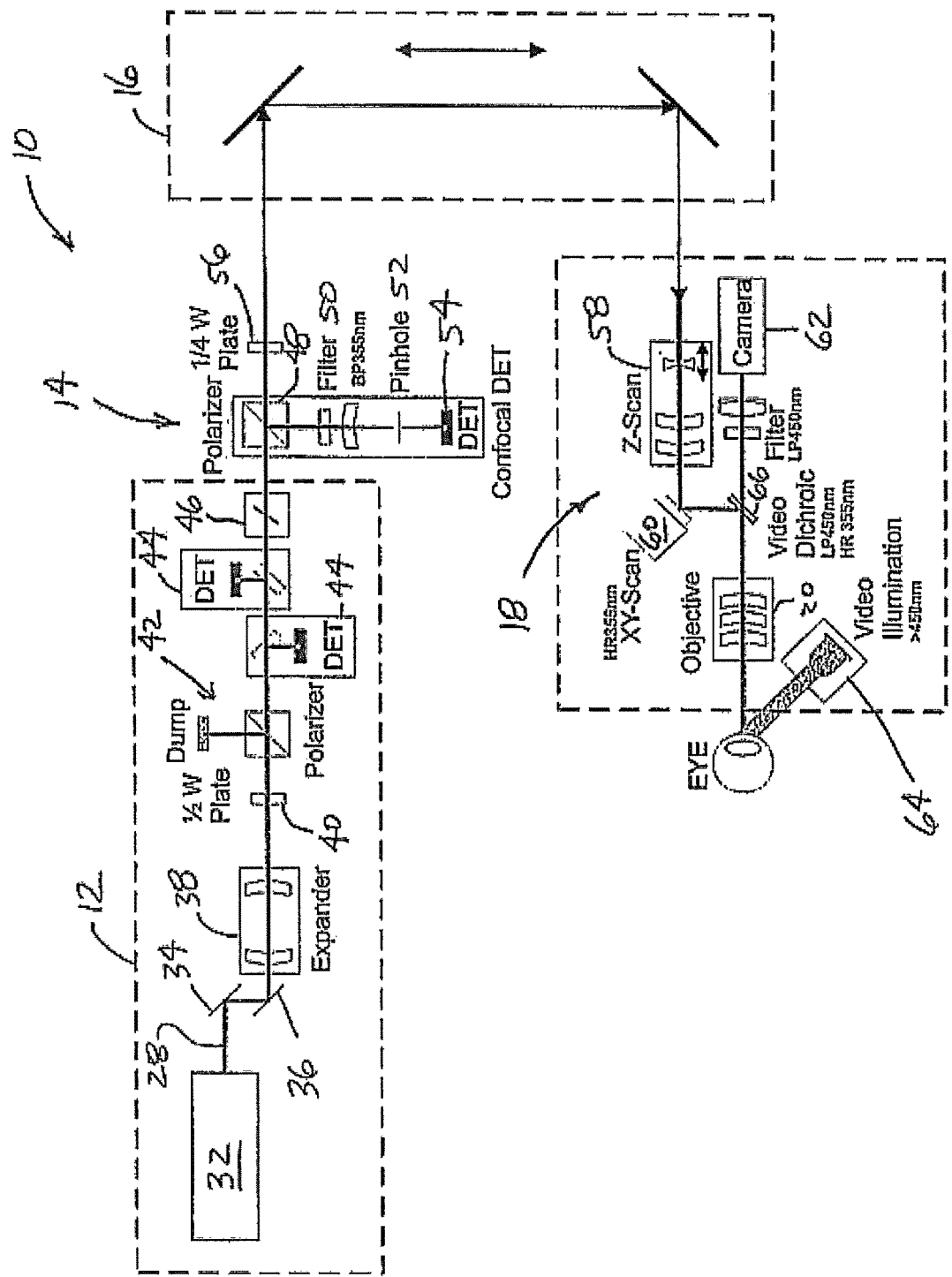
FIG. 2 is a schematic diagram of an embodiment of the laser surgery system of FIG. 1.

FIG. 2 schematically illustrates details of an embodiment of the laser surgery system 10. Specifically, exemplary configurations are schematically illustrated for the laser assembly 12, the confocal detection assembly 14, and the scanning assembly 18. As shown in the illustrated embodiment, the laser assembly 12 can include an ultrafast (UF) laser 32 (e.g., a femtosecond laser), alignment mirrors 34, 36, a beam expander 38, a half wave plate 40, a polarizer and beam dump device 42, output pickoffs and monitors 44, and a system-controlled shutter 46. The electromagnetic radiation beam 28 output by the laser 32 may be deflected by the alignment mirrors 34, 36. In many embodiments, the alignment mirrors 34, 36 may be adjustable in position and/or orientation so as to provide the ability to align the beam 28 with the downstream optical path through the downstream optical components. Next, the beam 28 may pass through the beam expander 38, which can increase the diameter of the beam 28. The expanded beam 28 may then pass through the half wave plate 40 before passing through the polarizer. The beam exiting the laser may be linearly polarized. The half wave plate 40 can rotate this polarization. The amount of light passing through the polarizer depends on the angle of the rotation of the linear polarization. Therefore, the half wave plate 40 with the polarizer may act as an attenuator of the beam 28. The light rejected from this attenuation may be directed into the beam dump. Next, the attenuated beam 28 may pass through the output pickoffs and monitors 44 and then through the system-controlled shutter 46. By locating the system-controlled shutter 46 downstream of the output pickoffs and monitors 44, the power of the beam 28 can be checked before opening the system-controlled shutter 46.

As shown in the illustrated embodiment, the confocal detection assembly 14 can include a polarization-sensitive device such as a polarized or an non-polarized beam splitter 48, a filter 50, a focusing lens 51, a pinhole aperture 52, and a detection sensor 54. A quarter wave plate 56 may be disposed downstream of the polarized beam splitter 48. The beam 28 received from the laser assembly 12 may be polarized so as to pass through the polarized beam splitter 48. Next, the beam 28 may pass through the quarter wave plate 56, thereby rotating the polarization axis of the beam 28. A quarter rotation may be a preferred rotation amount. After reflecting from a focal point in the eye, a returning reflected portion of the beam 28 may pass back through the quarter wave plate 56, thereby further rotating the polarization axis of the returning reflected portion of the beam 28. After passing back through the quarter wave plate 56, the returning reflected portion of the beam may experience a total polarization rotation of 90 degrees so that the reflected light from the eye may be fully reflected by the polarized beam splitter 48. A birefringence of the cornea can also be taken into account if, for example, the imaged structure is the crystalline lens. In this case, the plate 56 can be adjusted and/or configured so that the double pass of the plate 56 as well as the double pass of the cornea sum up to a polarization rotation of 90 degrees. Because the birefringence of the cornea may be different from patient to patient, the configuration/adjustment of the plate 56 can be done dynamically so as to optimize the signal returning to the detection sensor 54. In some embodiments, the plate 56 may be rotated at an angle. Accordingly, the returning reflected portion of the beam 28 may be polarized to be at least partially reflected by the polarized beam splitter 48 so as to be directed through the filter 50, through the lens 51, and to the pinhole aperture 52. The filter 50 can be configured to block wavelengths other than the wavelengths of interest. The pinhole aperture 52 may block any returning reflected portion of the beam 28 reflected from locations other than the focal point from reaching the detection sensor 54. Because the amount of returning reflected portion of the beam 28 that reaches the detection sensor 54 depends upon the nature of the tissue at the focal point of the beam 28, the signal generated by the detection sensor 54 can be processed in combination with data regarding the associated locations of the focal point so as to generate image/location data for structures of the eye.

As shown in the illustrated embodiment, the scanning assembly 18 can include a z-scan device 58 and a xy-scan device 60. The z-scan device 58 may be operable to vary a convergence/divergence angle of the beam 28 and thereby change a location of the focal point in the direction of propagation of the beam 28. For example, the z-scan device 58 can include one or more lenses that are controllably movable in the direction of propagation of the beam 28 to vary a convergence/divergence angle of the beam 28. The xy-scan device 60 may be operable to deflect the beam 28 in two dimensions transverse to the direction of propagation of the beam 28. For example, the xy-scan device 60 can include one or more mirrors that are controllably deflectable to scan the beam 28 in two dimensions transverse to the direction of propagation of the beam 28. Accordingly, the combination of the z-scan device 58 and the xy-scan device 60 can be operated to controllably scan the focal point in three dimensions, for example, within the eye of the patient.

As shown in the illustrated embodiment, a camera 62 and associated video illumination 64 can be integrated with the scanning assembly 18. The camera 62 and the beam 28 may share a common optical path through the objective lens assembly 20 to the eye. A video dichroic 66 may be used to combine and/or separate the beam 28 with and/or from the illumination wavelengths used by the camera. For example, the beam 28 can have a wavelength of about 355 nm and the video illumination 64 can be configured to emit illumination having wavelengths greater than 450 nm. Accordingly, the video dichroic 66 can be configured to reflect the 355 nm wavelength while transmitting wavelengths greater than 450 nm.

Figure 3:
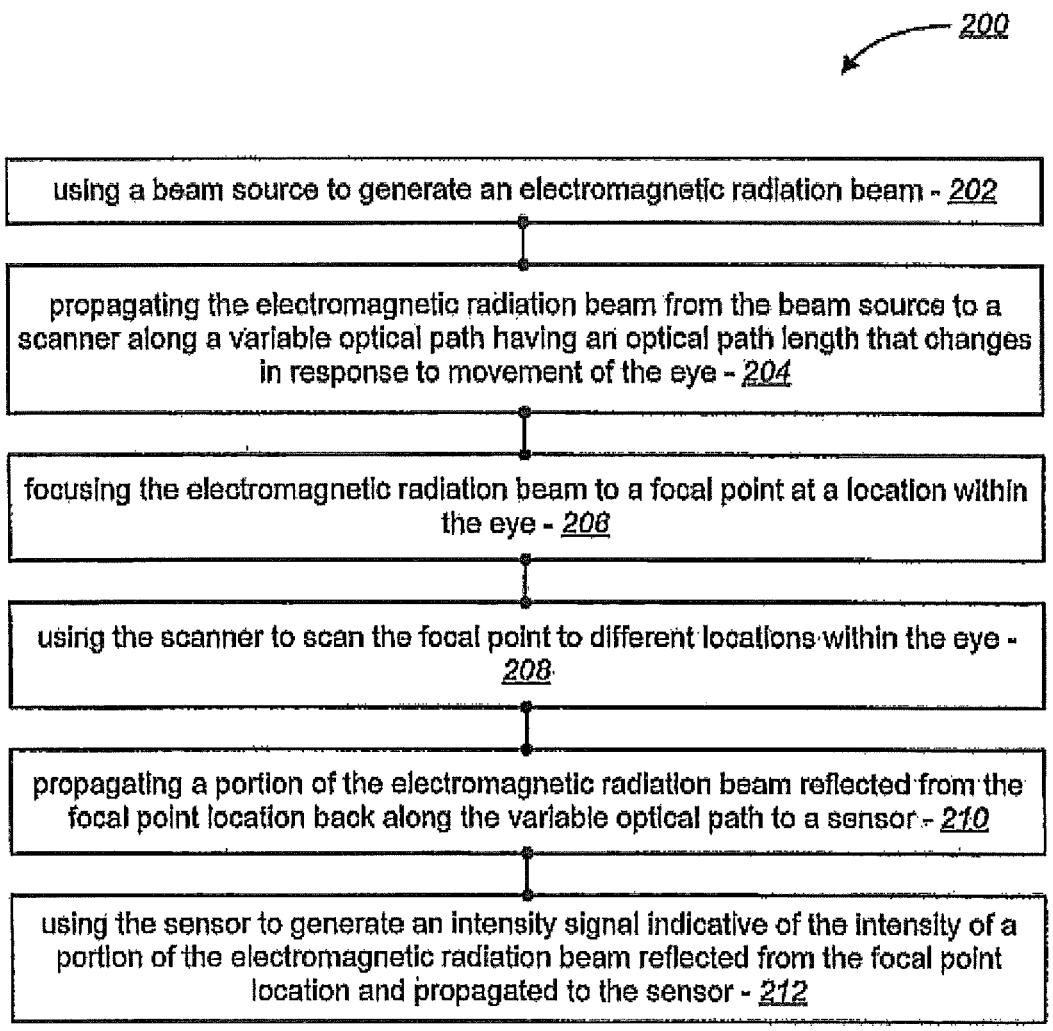
FIG. 3 is a simplified block diagram of acts of a method of imaging and/or of modifying an intraocular target according to many embodiments.

FIG. 3 is a simplified block diagram of acts of a method 200, according to many embodiments, of imaging an eye. Any suitable device, assembly, and/or system, such as that described herein, can be used to practice the method 200. The method 200 may include using a beam source to generate an electromagnetic radiation beam (act 202).

The method 200 may include propagating the electromagnetic radiation beam from a beam source to a scanner along a variable optical path having an optical path length that changes in response to movement of the eye (act 204). The method 200 may include focusing the electromagnetic radiation beam to a focal point at a location within the eye (act 206). The method 200 may include using the scanner to scan the focal point to different locations within the eye (act 208). The method 200 may include propagating a portion of the electromagnetic radiation beam reflected from the focal point location back along the variable optical path to a sensor (act 210). The method 200 may include using the sensor to generate an intensity signal indicative of the intensity of a portion of the electromagnetic radiation beam reflected from the focal point location and propagated to the sensor (act 212).

Figure 4:
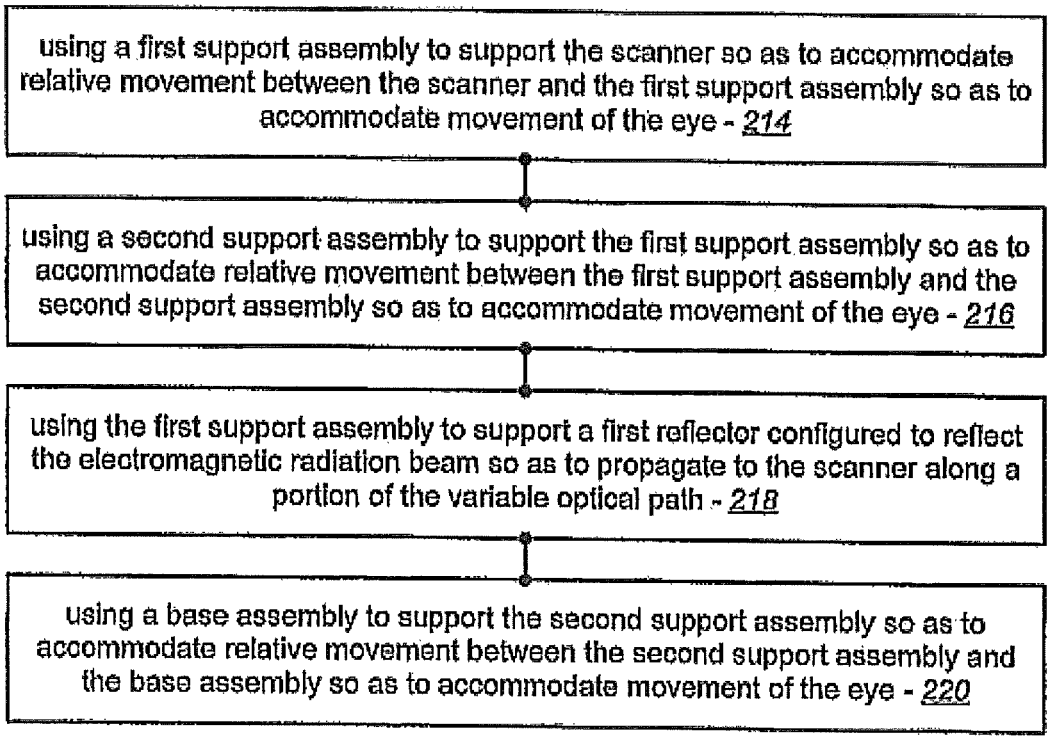

FIGS. 4, 5, and 6 are simplified block diagrams of optional acts that can be accomplished as part of the method 200. For example, the method 200 can include using a first support assembly to support the scanner so as to accommodate relative movement between the scanner and the first support assembly so as to accommodate movement of the eye (act 214). The method 200 can include using a second support assembly to support the first support assembly so as to accommodate relative movement between the first support assembly and the second support assembly so as to accommodate movement of the eye (act 216). The method 200 can include using the first support assembly to support a first reflector configured to reflect the electromagnetic radiation beam so as to propagate to the scanner along a portion of the variable optical path (act 218). The method 200 can include using a base assembly to support the second support assembly so as to accommodate relative movement between the second support assembly and the base assembly so as to accommodate movement of the eye (act 220). The method 200 can include using the second support assembly to support a second reflector configured to reflect the electromagnetic radiation beam to propagate along a portion of the variable optical path so as to be incident on the first reflector (act 222). The method 200 can include using the sensor to generate the intensity signal comprises passing a reflected portion of the electromagnetic radiation beam through an aperture to block portions of the electromagnetic radiation beam reflected from locations other than the focal point location (act 224). The method 200 can include passing the electromagnetic radiation beam through a polarization-sensitive device (act 226). The method 200 can include modifying polarization of at least one of the electromagnetic radiation beam and a portion of the electromagnetic radiation beam reflected from the focal point location (act 228). The method 200 can include using the polarization-sensitive device to reflect a portion of the electromagnetic radiation beam reflected from the focal point location so as to be incident upon the sensor (act 230).

Figure 7:
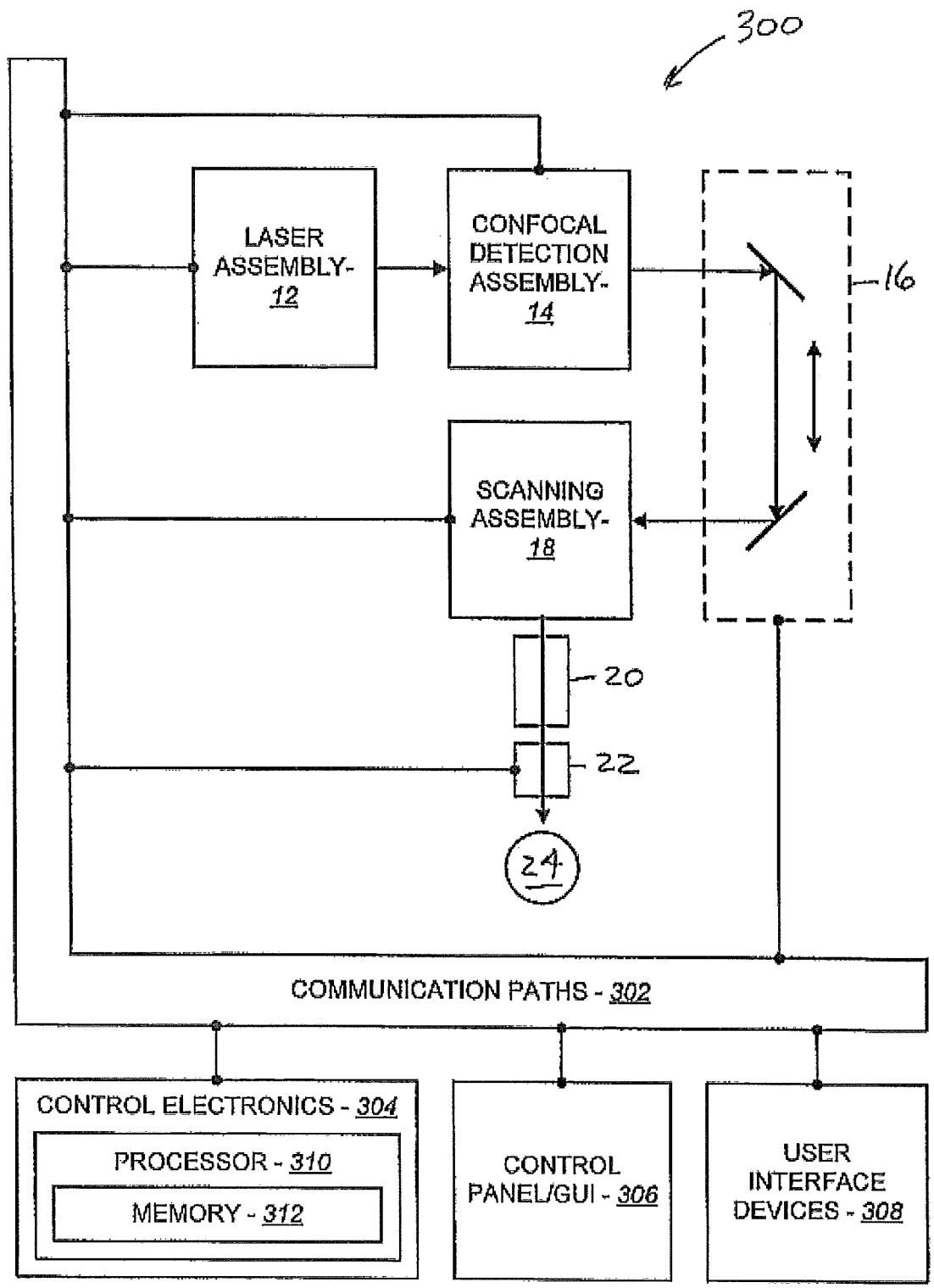
FIG. 7 is a schematic diagram of an embodiment of the laser surgery system of FIG. 1.

FIG. 7 schematically illustrates a laser surgery system 300, according to many embodiments. The laser surgery system 300 includes the laser assembly 12, the confocal detection assembly 14, the free-floating mechanism 16, the scanning assembly 18, the objective lens assembly 20, the patient interface 22, communication paths 302, control electronics 304, control panel/graphical user interface (GUI) 306, and user interface devices 308. The control electronics 304 includes processor 310, which includes memory 312. The patient interface 22 is configured to interface with a patient 24. The control electronics 304 is operatively coupled via the communication paths 302 with the laser assembly 12, the confocal detection assembly 14, the free-floating mechanism 16, the scanning assembly 18, the control panel/GUI 306, and the user interface devices 308.

The scanning assembly 18 can include a z-scan device and a xy-scan device and a camera. The laser surgery system 300 can be configured to focus the electromagnetic radiation beam 28 to a focal point that is scanned in three dimensions. The z-scan device can be operable to vary the location of the focal point in the direction of propagation of the beam 28. The xy-scan device can be operable to scan the location of the focal point in two dimensions transverse to the direction of propagation of the beam 28. Accordingly, the combination of the z-scan device and the xy-scan device can be operated to controllably scan the focal point of the beam in three dimensions, including within a tissue of the patient 24 such as within an eye tissue of the patient 24. The scanning assembly 18 may be supported by the free-floating mechanism 16, which may accommodate patient movement induced movement of the scanning assembly 18 relative to the laser assembly 12 and the confocal detection assembly 14 in three dimensions.

The patient interface 22 is coupled to the patient 24 such that the patient interface 22, the objective lens assembly 20, and the scanning assembly 18 move in conjunction with the patient 24. For example, in many embodiments, the patient interface 22 employs a suction ring that is vacuum attached to an eye of the patient 24. The suction ring can be coupled with the patient interface 22, for example, using vacuum to secure the suction ring to the patient interface 22.

The control electronics 304 controls the operation of and/or can receive input from the laser assembly 12, the confocal detection assembly 14, the free-floating assembly 16, the scanning assembly 18, the patient interface 22, the control panel/GUI 306, and the user interface devices 308 via the communication paths 302. The communication paths 302 can be implemented in any suitable configuration, including any suitable shared or dedicated communication paths between the control electronics 304 and the respective system components.

The control electronics 304 can include any suitable components, such as one or more processor, one or more field-programmable gate array (FPGA), and one or more memory storage devices. In many embodiments, the control electronics 304 controls the control panel/GUI 306 to provide for pre-procedure planning according to user specified treatment parameters as well as to provide user control over the laser eye surgery procedure.

The control electronics 304 can include a processor/controller 310 that is used to perform calculations related to system operation and provide control signals to the various system elements. A computer readable medium 312 is coupled to the processor 310 in order to store data used by the processor and other system elements. The processor 310 interacts with the other components of the system as described more fully throughout the present specification. In an embodiment, the memory 312 can include a look up table that can be utilized to control one or more components of the laser system surgery system 300.

The processor 310 can be a general purpose microprocessor configured to execute instructions and data, such as a Pentium processor manufactured by Intel Corporation of Santa Clara, California. It can also be an Application Specific Integrated Circuit (ASIC) that embodies at least part of the instructions for performing the method according to the embodiments of the present disclosure in software, firmware and/or hardware. As an example, such processors include dedicated circuitry, ASICs, combinatorial logic, other programmable processors, combinations thereof, and the like.

The memory 312 can be local or distributed as appropriate to the particular application. Memory 312 can include a number of memories including a main random access memory (RAM) for storage of instructions and data during program execution and a read only memory (ROM) in which fixed instructions are stored. Thus, the memory 312 provides persistent (non-volatile) storage for program and data files, and may include a hard disk drive, flash memory, a floppy disk drive along with associated removable media, a Compact Disk Read Only Memory (CD-ROM) drive, an optical drive, removable media cartridges, and other like storage media.

The user interface devices 308 can include any suitable user input device suitable to provide user input to the control electronics 304. For example, the user interface devices 308 can include devices such as, for example, a touch-screen display/input device, a keyboard, a footswitch, a keypad, a patient interface radio frequency identification (RFID) reader, an emergency stop button, and a key switch.

System Calibration

The laser surgery system 10 can be calibrated to relate locations in a treatment space with pixels in the camera 62 and with control parameters used to control the scanning assembly 18 such that the focal point of the electromagnetic radiation beam can be accurately positioned within the intraocular target. Such calibration can be accomplished at any suitable time, for example, prior to using the laser surgery system 10 to treat a patient's eye.

Figure 8:
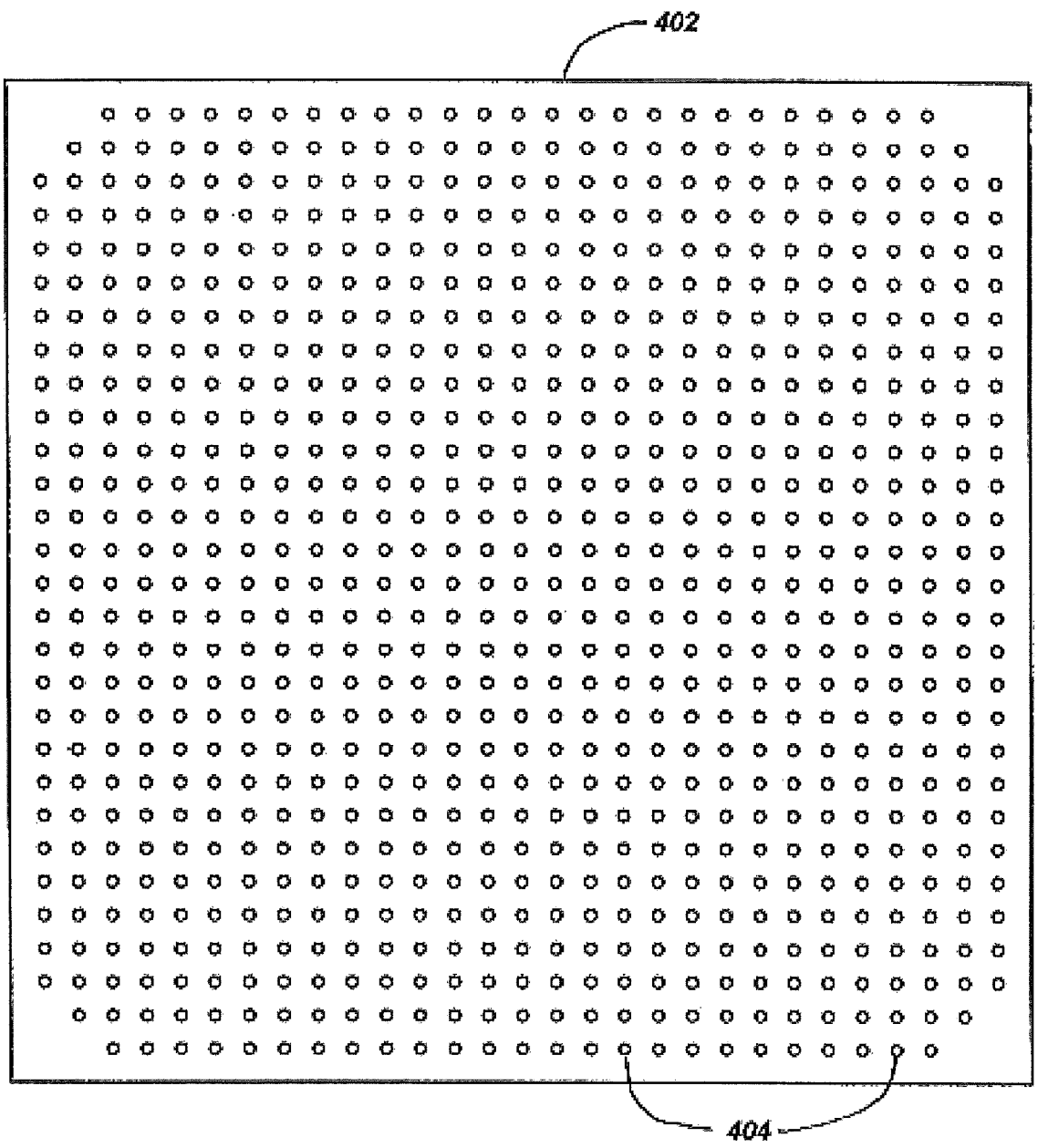
FIG. 8 is a plan view illustrating a calibration plate that can be used to calibrate the laser surgery system of FIG. 1 according to many embodiments.

FIG. 8 is a top view diagram of a calibration plate 402 that can be used to calibrate the laser surgery system 10. In many embodiments, the calibration plate 402 is a thin plate having an array of target features, for example, through holes 404 therein. In alternate embodiments, the calibration plate 402 is a thin plate having a field of small dots as the target features. While any suitable arrangement of the target features can be used, the calibration plate 402 of FIG. 8 has an orthogonal array of through holes 404. Any suitable number of the target features can be included in the calibration plate 402. For example, the illustrated embodiment has 29 rows and 29 columns of the through holes 404, with three through holes at each of the four corners of the calibration plate 402 being omitted from the orthogonal array of through holes 404.

In many embodiments, each of the through holes 404 is sized small enough to block a suitable portion of an electromagnetic radiation beam when the focal point of the electromagnetic radiation beam is not located at the through hole. For example, each of the through holes 404 can have a diameter slightly greater than the diameter of the focal point of the electromagnetic radiation beam so as to not block any of the electromagnetic radiation beam when the focal point is positioned at one of the through holes 404. In the embodiment shown, the through holes 404 have a diameter of 5 µm, which is sized to be used in conjunction with a focal point diameter of 1 µm.

Figure 9:
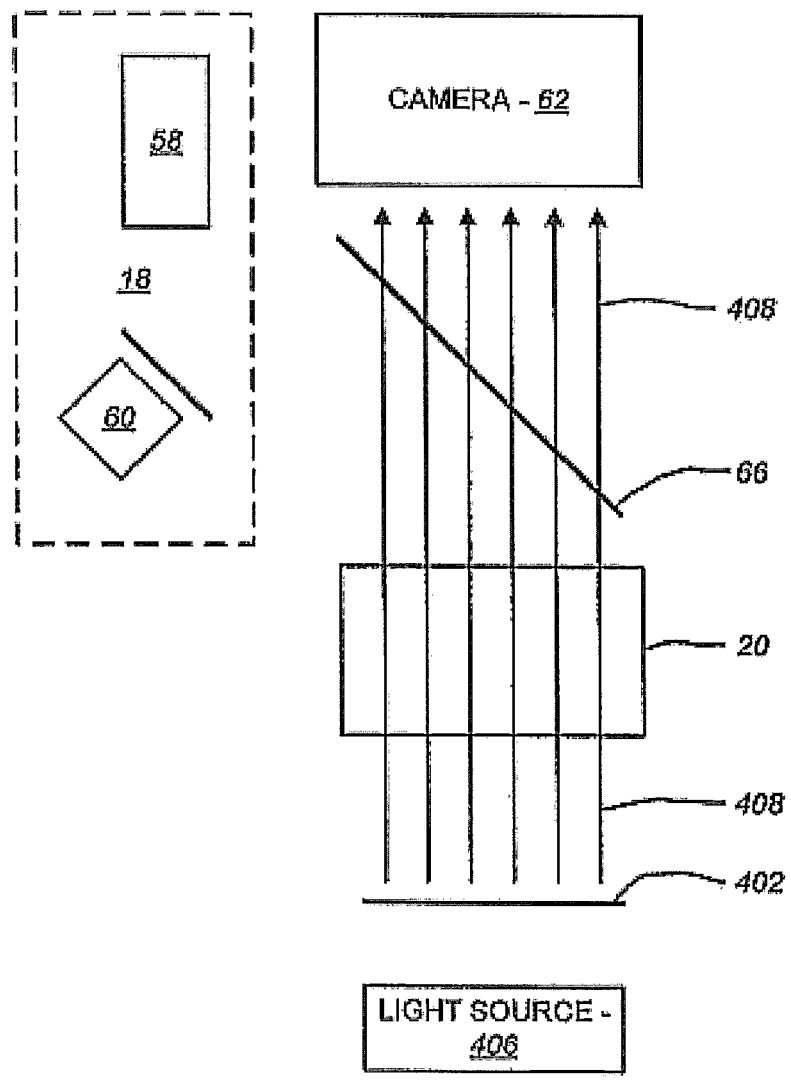
FIG. 9 is a schematic diagram illustrating using the calibration plate of FIG. 8 to calibrate a camera of the laser surgery system of FIG. 1.

FIG. 9 schematically illustrates using the calibration plate 402 to calibrate the camera 62 of the laser surgery system 10. The calibration plate 402 is supported at a known fixed location relative to the objective lens assembly 20. In many embodiments, the objective lens assembly 20 is configured for telecentric scanning of the electromagnetic radiation beam and the calibration plate 402 is supported to be perpendicular to the direction of propagation of the electromagnetic radiation beam. The calibration plate 402 is disposed between the objective lens assembly 20 and a light source 406. The light source 406 is used to illuminate the calibration plate 402. A portion of the illumination light from the light source 406 passes through each of the through holes 404, thereby producing an illuminated location within the field of view of the camera 62 at each of the through holes 404. A light beam 408 from each of the through holes 404 passes through the objective lens assembly 20, through the video dichroic 66, an into the camera 62. In many embodiments, the camera 62 includes a sensor having an orthogonal array of pixels (e.g., in x and y directions where the corresponding z direction is in the direction of propagation of the electromagnetic radiation beam). In many embodiments, X and Y pixel values for each of the light beams 408 is used in conjunction with the known locations of the through holes 404 relative to the objective lens assembly 20 to determine the relationship between the camera X and Y pixel values and locations in the treatment space for dimensions transverse to the propagation direction of the electromagnetic radiation beam.

Figure 10:
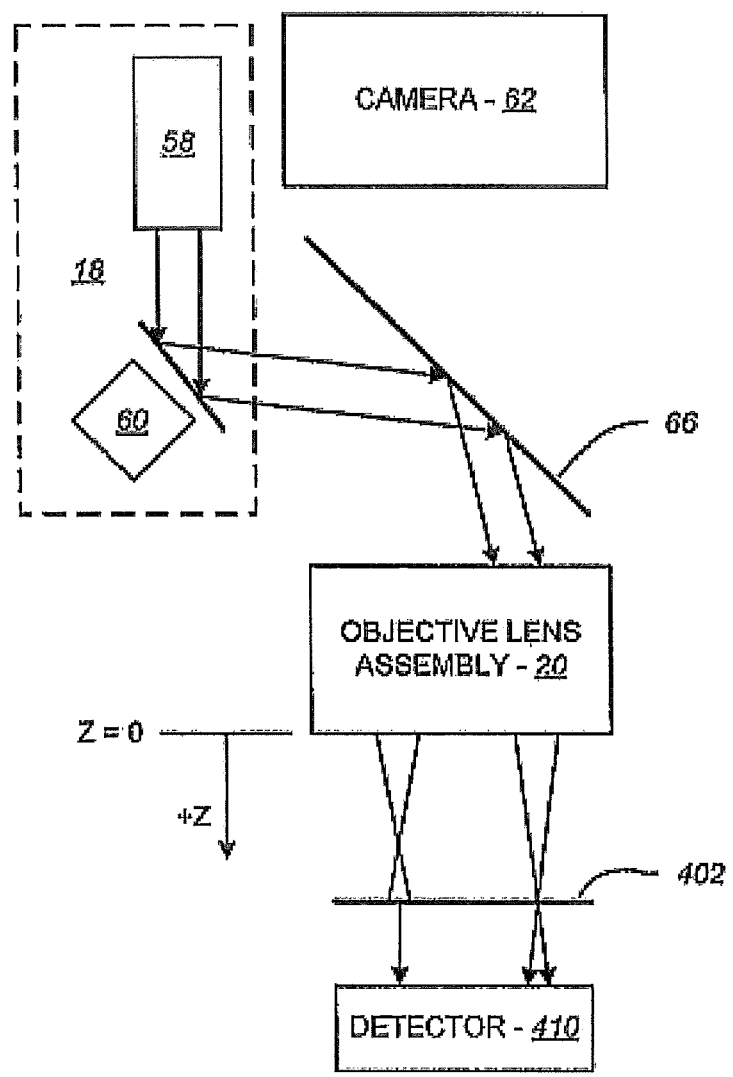
FIG. 10 is a schematic diagram illustrating using the calibration plate of FIG. 8 to calibrate the scanning assembly of the laser surgery system of FIG. 1.

FIG. 10 schematically illustrates using the calibration plate 402 to calibrate the scanning assembly 18. The calibration plate 402 is supported at a known fixed location relative to the objective lens assembly 20. In many embodiments, the objective lens assembly 20 is configured for telecentric scanning of the electromagnetic radiation beam and the calibration plate 402 is supported to be perpendicular to the direction of propagation of the electromagnetic radiation beam. The calibration plate 402 is disposed between the objective lens assembly 20 and a detector 410. The detector 410 is configured to generate a signal indicative of how much of the electromagnetic radiation beam is incident thereon, thereby being indirectly indicative of how much of the electromagnetic radiation beam is blocked by the calibration plate 402. For example, when the focal point of the electromagnetic radiation beam is positioned at one of the through holes 404 (as illustrated for the focal point disposed on the right side of the detection plate 402 in FIG. 10), a maximum amount of the electromagnetic radiation beam passes through the through hole and is incident on the detector 410. In contrast, when the focal point of the electromagnetic radiation beam is not positioned at one of the through holes 404 (as illustrated for the focal point disposed above the left side of the detection plate 402 in FIG. 10), a portion of the electromagnetic radiation beam is blocked from reaching the detector 410.

Control parameters for the z-scan device 58 and the xy-scan device 60 are varied to locate the focal point of the electromagnetic radiation beam at each of a suitable set of the through holes, thereby providing data used to determine the relationship between the control parameters for the scanning assembly 18 and the resulting location of the focal point of the electromagnetic radiation beam. The z-scan device 58 is operable to vary a convergence or divergence angle of the electromagnetic radiation beam, thereby being operable to control the distance of the focal point from the objective lens in the direction of propagation of the electromagnetic radiation beam. The xy-scan device 60 is operable to vary a direction of the electromagnetic radiation beam in two dimensions, thereby providing the ability to move the focal point in two dimensions transverse to the direction of propagation of the electromagnetic radiation beam.

A suitable existing search algorithm can be employed to vary the control parameters for the z-scan device 58 and the xy-scan device 60 so as to reposition the focal point to be located at each of a suitable set of the through holes 404. In many embodiments where the objective lens assembly 20 is configured to telecentrically scan the electromagnetic radiation beam, the resulting control parameter data for the scanning assembly 18 can be used to calibrate the scanning assembly 18 relative to directions transverse to the direction of propagation of the electromagnetic radiation beam (e.g., x and y directions transverse to a z direction of propagation of the electromagnetic radiation beam).

Figure 11:
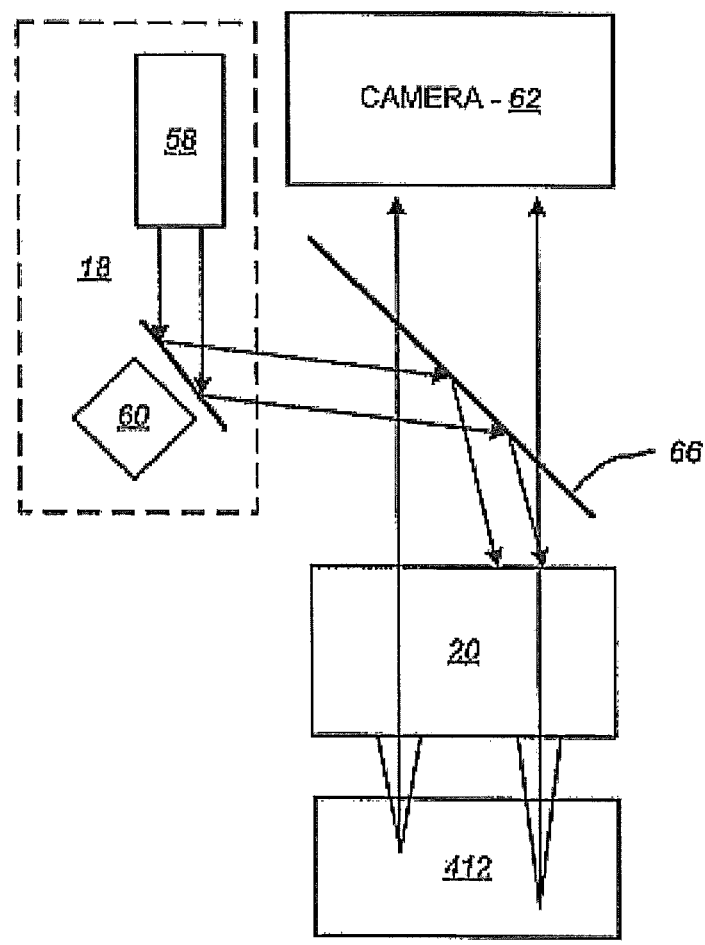
FIG. 11 is a schematic diagram illustrating using a fluorescent material to calibrate the scanning assembly of the laser surgery system of FIG. 1.

FIG. 11 schematically illustrates using a fluorescent material block 412 to calibrate the scanning assembly 18. The fluorescent material block 412 is made of a suitable fluorescent material that emits light in response to absorbing electromagnetic radiation. The fluorescent material block 412 is supported at a fixed location relative to the objective lens assembly 20. With the focal point of the electromagnetic radiation beam disposed within the block 412, the camera 62 is used to observe the location of the resulting fluorescent emission in the block 412. The observed location of the resulting fluorescent emission can be used in conjunction with calibration data for the camera 62 to determine x and y coordinates of the associated focal point in the treatment space. Suitable variation in the location of the focal point within the fluorescent material block 412 and associated position data for the resulting fluorescent emissions generated via the camera 62 can be used to calibrate the control parameters for the scanning assembly 18. For example, in embodiments where the objective lens assembly 20 is configured to telecentrically scan the focal point, the corresponding positional data for the resulting fluorescent emissions can be used to generate calibrated control parameters for the xy-scan device 60 for positioning the focal point transverse to the direction of propagation of the electromagnetic radiation beam.

Figure 12:
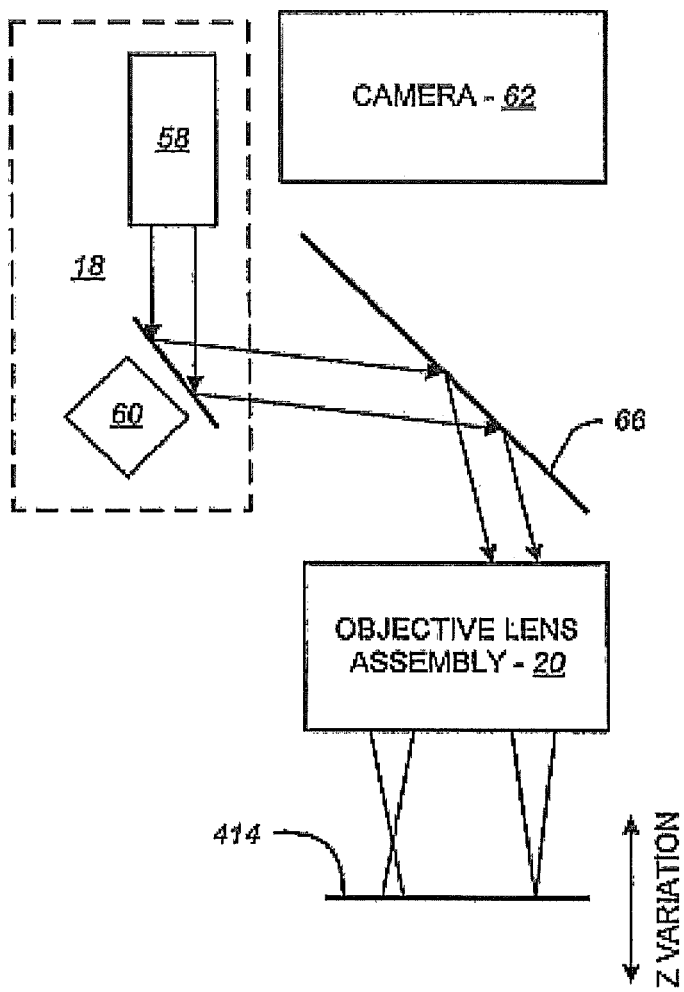
FIG. 12 is a schematic diagram illustrating using a repositionable reflective surface to calibrate the scanning assembly of the laser surgery system of FIG. 1.
Figure 13:
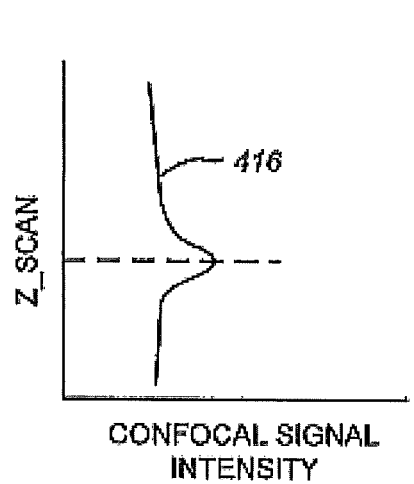
FIG. 13 illustrates variation in intensity of a signal generated using the reflective surface of FIG. 12 relative to a control parameter for a z-scan device of the laser surgery system of FIG. 1.

FIG. 12 schematically illustrates the use of a reflective member 414 to calibrate the scanning assembly 18. The reflective member 414 is supported at a suitable plurality of known fixed distances relative to the objective lens assembly 20. In many embodiments, the objective lens assembly 20 is configured for telecentric scanning of the electromagnetic radiation beam and the reflective member 414 is supported to be perpendicular to the direction of propagation of the electromagnetic radiation beam. The reflective member 414 reflects the electromagnetic radiation beam back through the objective lens assembly 20, back through the scanning assembly 18, back through the free-floating mechanism 16, and back to the confocal detection assembly 14. For a particular distance between the objective lens assembly 20 and the reflective member 414, the z-scan device 58 can be operated to vary the distance of the focal point from objective lens assembly. Alternatively, for a particular setting of the z-scan device resulting in a particular distance of the focal point from the objective lens assembly, the distance between the objective lens assembly 20 and the reflective member 414 can be varied. As illustrated in FIG. 13, a resulting signal 416 produced by the detection sensor 54 of the confocal detection assembly 14 varies in intensity with variation in the distance between the focal point and the reflective member 414. The intensity of the signal 416 generated by the detection sensor 54 is maximized when the focal point is located at the surface of the reflective member 414, thereby maximizing the amount of reflected light that passes through the pinhole aperture 52 to reach the detection sensor 54. By determining the values of the control parameter for the z-scan device 58 corresponding to a suitable plurality of distances between the reflective member 414 and the objective lens assembly 20, suitable calibration parameters can be generated for use in controlling the z-scan device 58 to control the location of the focal point in the treatment space in the direction of propagation of the electromagnetic radiation beam.

In some embodiments methods and apparatus for providing adjustment to compensate for variations in disposable elements and other attachments, tolerances in hardware and alignment, and patient anatomy. The methods and apparatus may comprise a software look up table (hereinafter "LUT") embodied in a tangible medium. The LUT may comprise a map of locations of the cutting volume in order to the control of actuators that direct the ranging (target detection) and the cutting modalities. A baseline LUT can be generated for a generalized system using optical based rules and physics, detailed modeling of components, and anchoring (one time) to a finite data set as described herein. The expected variations can be reduced into a set of finite and manageable variables that are applied to modify the tables subsequent to the original generation of the tables. For a constructed system having constructed components with manufacturing tolerances, fine tuning and modification of the LUTs can be achieved thru simple modifications of the tables based on individual system and automated measurements. These individualized measurements of a constructed system can be applied to variations due to one or more of: tool-to-tool variation, tool to itself variation (for example align variations), output attachment variations (for example disposable contact lenses), or patient to patient (for example individual patient anatomy), and combinations thereof, for example.

In many embodiments, one or more of the following steps can be performed with the processor and methods as described herein. For example, baseline LUT generation can be performed comprising mapping and position detection in order to provide actuator commands to evaluate system output performance. A baseline transfer function can be generated for a patient coordinate reference system such as XYZ to detect actuators of the system, for example. Baseline LUT generation can be performed to map cutting to actuators. A transfer function can be generated for XYZ to cutting actuators, for example. Baseline LUTs (transfer functions) can be generated via model (ray trace), data, or a combination, for example. The baseline LUTs can be modified given variations in the system, disposable, eye, application, for example. The baseline LUT modification may comprise an adjustment to the baseline LUT, for example. The baseline LUT modification may comprise a software (hereinafter "SW") adjustment to compensate for hardware (hereinafter "HW") variations, for example. The LUT modification as described herein can extend surgical volume, so as to treat the cornea, the limbus and the posterior capsule, either in lateral extent, axial extent, and resolution, for example. The LUT methods and apparatus can enable switching in tools for calibration and other optical components to accessorize—output attachments, for example. The LUT can be set up so that the system is capable of measuring location of attachments at two surfaces and then can accurately place cuts in targeted material volume based on modifying the baseline LUT using this the locations of the two surfaces, for example. The LUTS can provide more cuts ranging from lens, capsule, corneal incisions for cataract, cornea flaps, for example. The different sub-systems as described herein can have separate LUTS, which can be combined with calibration process as described herein, for example.

Whether alternatively or in combination, the same subsystem can be used for both ranging and cutting. The UF system can be used at a low power level to find surfaces and then used at high power for cutting, for example. The LUTs can be used such that the location mode differs from the cutting mode. In some instances, the cut locations can differ based on changes with power level, and the cut location may not occur at focus when the energy per pulse substantially exceeds the threshold amount of energy.

In many embodiments, the LUTs of the methods and apparatus as described herein follow these principles. The baseline LUT can generated by ray tracing and data anchoring using specific tooling, for example. In many embodiments, each optically transmissive structure of the patient interface, such as a lens, is read by the system to determine its thickness and location. These numbers can be used to modify the LUTS to attain <100 μm accuracy, for example.

In many embodiments, the LUTs of the methods and apparatus as described herein are also modified to account for alignment tilts, contact lens mounting, contact lens variations so as to achieve <100 μm accuracy on cuts, for example. In many embodiments, a bubbles in plastic flatness test with the calibration apparatus as described herein generates offset and tilt adjustments of baseline UF LUT.

In many embodiments, the baseline component specifications may be less than ideal for delivering an appropriate system performance, and the final performance can be refined using SW corrections and factors based on the components of the individual system which can be determined from optically-grounded data-anchored baseline LUTs further modified for enhanced performance, for example.

A feedback loop can be used to build the enhanced or modified LUTs for the individual laser system, for example. The feedback methods and apparatus as described herein can allow SW adjustments based on LUTs and other SW factors that may not be corrected with hardware alignment, for example.

The LUTs and the methods an apparatus configured to modify the look up tables so as to enhance system performance can provide an improvement within the 3D surgical volume as described herein. The methods and apparatus as described herein can provide improved surgery for more patients with a level of high performance. The methods and apparatus such as those described herein can provide high performance using off-the-shelf components, such as high-volume, low-cost components to make surgical procedures available to greater numbers of patients.

Figure 14:
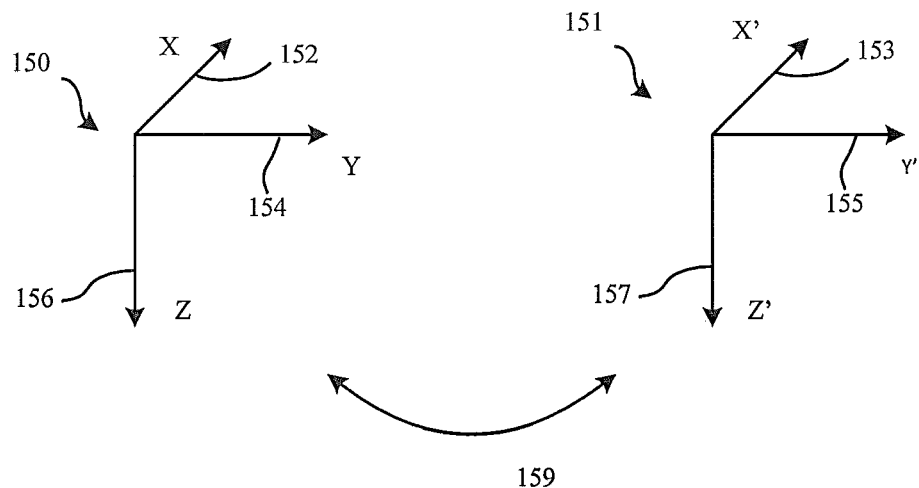
FIG. 14 shows mapping of coordinate references from an eye space coordinate reference system to a machine coordinate reference system, according to many embodiments.

FIG. 14 shows mapping of coordinate references from an eye space coordinate reference system 150 to a machine coordinate reference system 151 so as to coordinate the machine components with the physical locations of the eye. Physical coordinates of the eye may be mapped to machine coordinates of the components as described herein. The eye space coordinate reference system 150 may comprise a first X dimension 152, for example an X axis, a second Y dimension 154, for example a Y axis, and a third Z dimension 156, for example a Z axis. Optionally, the coordinate reference system of the eye may comprise one or more of many known coordinate systems such as polar, cylindrical or Cartesian. In many embodiments, the reference system 150 comprises a right handed triple with the X axis oriented in a nasal temporal direction on the patient, the Y axis oriented superiorly on the patient and the Z axis oriented posteriorly on the patient. In many embodiments, the corresponding machine coordinate reference system 151 comprises a first X' dimension 153, a second Y' dimension 155, and a third Z' dimension 157 generally corresponding to machine actuators, and the coordinate reference system of the machine may comprise one or more of many known coordinate systems such as polar, cylindrical or Cartesian, and combinations thereof, for example.

The machine coordinate reference 151 may correspond to locations of one or more components of a laser system. The machine coordinate reference system 151 may comprise a plurality of machine coordinate reference systems. The plurality of machine coordinate references system s may comprise a coordinate reference system for each subsystem, for example. The axes of the machine coordinate reference system may be combined in one or more of many ways. In some embodiments, the locations of the components of the laser system may be combined in order to map the plurality of machine coordinate reference systems to the coordinate reference system 150 of the eye.

Figure 15:
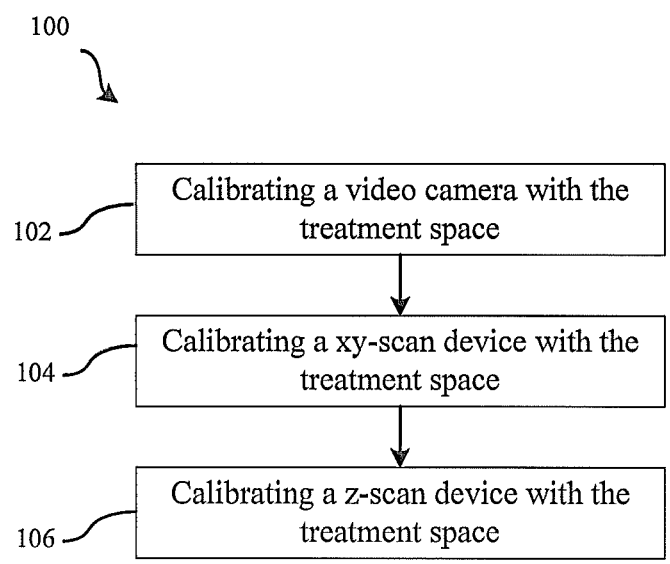
FIG. 15 illustrates an exemplary method for calibrating a laser system according to some embodiments of the invention.

FIG. 15 illustrates a simplified block diagram of acts of a method 100 for calibrating a laser system. The laser system may include a video camera, an xy-scan device for scanning an electromagnetic radiation beam to locations orthogonal to the beam's propagation and a z-scan device for focusing a focal point of an electromagnetic radiation beam to different distances from the laser system. At step 102, the video camera may be calibrated with coordinates in the treatment space. At step 104, a xy-scan device may be calibrated with the treatment space and at step 106, the z-scan device may be calibrated with the treatment space.

Figure 16:
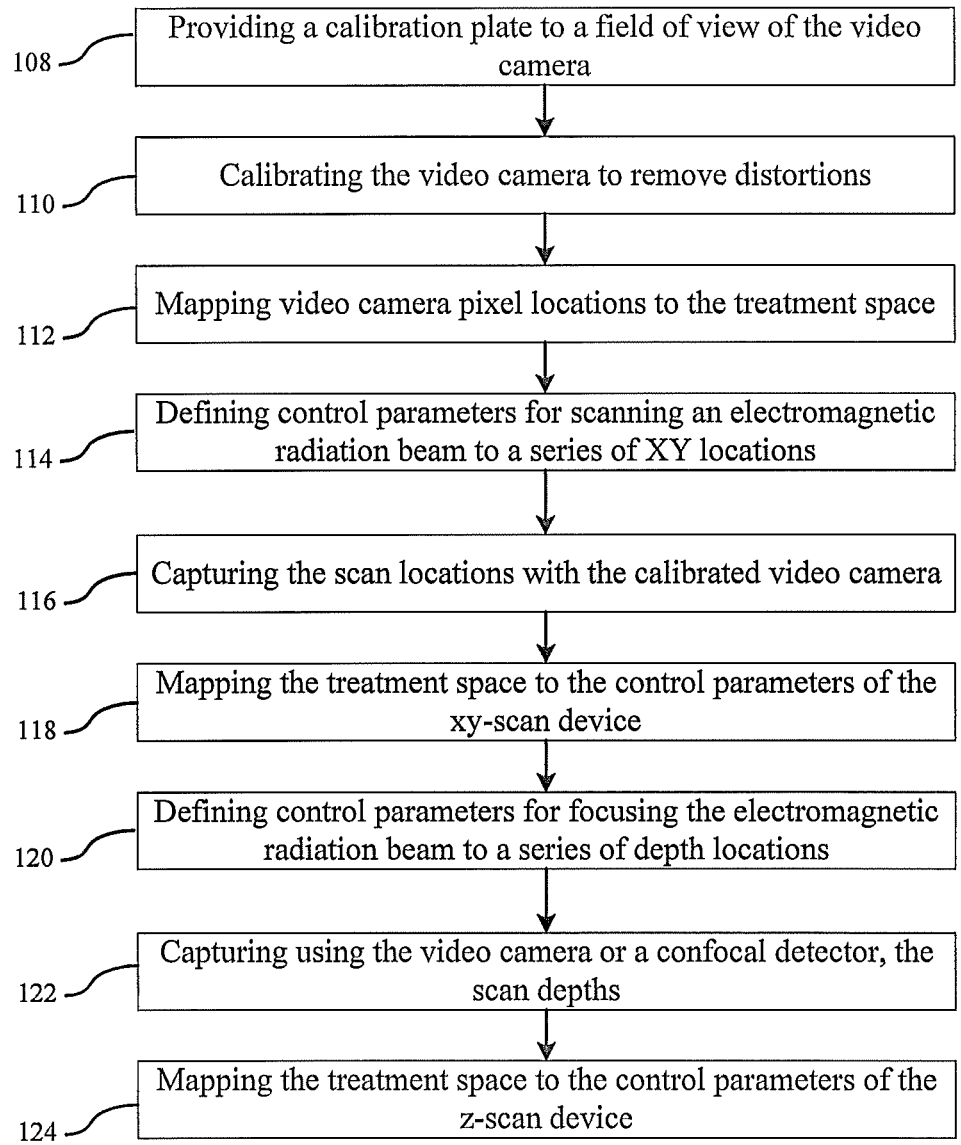
FIG. 16 is a simplified block diagram of optional acts that can be accomplished in the method of FIG. 15 according to many embodiments.

FIG. 16 shows simplified block diagrams of optional acts that can be used to accomplished some or all steps of the method 100. For example, the video camera may be calibrated 102 with the treatment space by providing a calibration plate to a field of view of the video camera 108. The video camera imaging system may use a telecentric lens to provide and orthographic view of the calibration plate. By viewing a calibration plate, the video camera image data may be processed to remove distortions in the video camera system 110. At step 112, the video camera may be calibrated with the treatment space 102 by mapping the video camera pixel locations to locations in the treatment space. The mapping may be primarily a two-dimensional mapping of Xm, Ym to X, Y. Because of the large depth of field of the imaging path and the telecentric form, the Z location may remain unchanged for the range of Z for which the image is in focus. In some embodiments, the camera can be a suitable imaging device for any silicon based detector array of the appropriately sized format. A video lens may form an image onto a camera detector array while optical elements provide polarization control and wavelength filtering respectively. An aperture or iris provides control of imaging and therefore depth of focus and depth of field and resolution. A small aperture may provide the advantage of large depth of field that aids in the patient docking procedure. In some instances, the video camera image sensor may comprise X and Y pixels, Pix X and Pix Y, respectively. The dimension 153 of the machine coordinate reference 151 may correspond to X pixels of the video camera. The dimension 155 may correspond to Y pixels of the camera. In some embodiments, the video camera pixel locations may be mapped using a system specific look up table to generate pixel locations corresponding to the treatment space. Optionally, polynomial fitting may be used to map pixel locations to physical locations in the treatment space.

Figure 17:
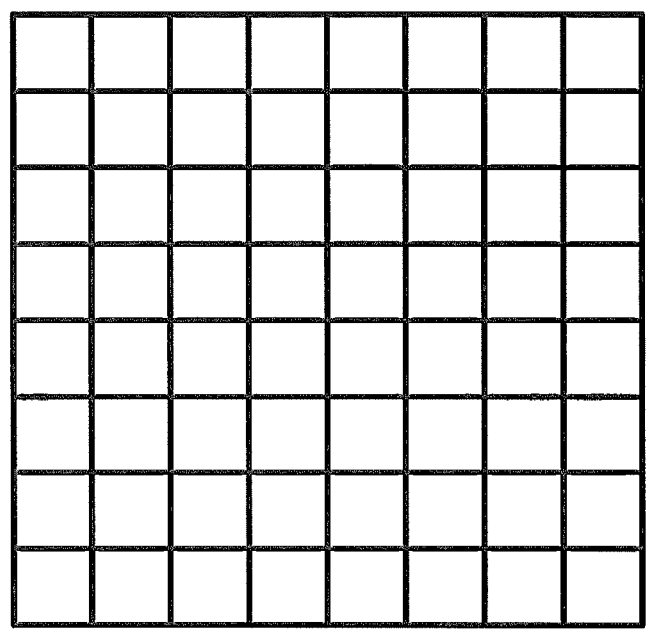
FIG. 17 illustrates a configuration of a calibration plate that may be used to calibrate a video camera of a laser system according to embodiments of the invention.

FIG. 17 illustrates an exemplary calibration plate that comprises a calibration grid 1700. The calibration grid 1700 may define known locations in the treatment space. In some situations, the spacing and/or intersections 1710 of the grid may define the know locations. In other embodiments, the calibration plate shown in FIG. 8 may be used for calibrating the video camera system. After distortions of the video camera system are removed, polynomial or other fitting such as look up tables can be used to map video camera pixel locations to physical locations in the treatment space. In some embodiments, computer algorithms may be used to automatically locate grid intersections 1710 or the through holes 404 of a calibration plate.

FIG. 18 shows an exemplary look up table 330 for a video camera. The look up table 330 may comprise a plurality of discrete input values 332 over a range, for example, four values such as X, Y, Z of patient coordinate reference system and distance CL of the lower surface of the lens, and a plurality of discrete output values 334. The X and Y values of the eye can range from −9 to 9 mm, in 1 mm increments, for example. The Z value can range from 6 to 10 mm in 1 mm increments, for example. The CL value can range from −1 to 1 mm in 0.5 mm increments, for example. These four dimensional input values can be input into processor system and an output machine value provide for each combined input. The output values 334 of the look up table can be provided as Pixel X, Pixel Y, and the range of Pixel X and Pixel Y can each be from about −543 pixels to about 543 pixels. The output and input mapping process can be switched. The video system is a measurement device used to find intended surfaces. The video system is also used as target aid for the user to place cuts. In these ways, the values of Pixel X and Pixel Y are determined using the video image. The values of Pixel X and Pixel Y along with either assumptions or measurements made for Z and CL are used as input values to generate output values for X, Y, and Z for the location of the intended targeted structure.

The data for each look up table can be interpolated, for example with known interpolation methods. For example, the interpolation may comprise linear interpolation based on values of closest neighbors provided to the look up table. The look up table can be extrapolated to extend the ranges.

The look up tables as described herein are provided according to examples, and a person of ordinary skill in the art will recognize many alternatives and variations.

FIG. 19 shows an optical schematic of the components corresponding to the look up table of FIG. 18. The optical system forms an image on the camera array comprising x pixels at x pixel locations (hereinafter "Pix X") and y pixels at y pixel locations (hereinafter Pix Y). The image is formed with a plurality of fixed focus lenses. The image beam passes through an aperture stop located between the fixed focus lenses to arrive at the sensor array. A field stop is provided along with another fixed focus lens optically coupled to the objective lenses. The patient interface and distances are described herein.

FIG. 20 shows input and output of the look up table as in FIGS. 18 and 19. The input comprises the measured Pix X and Pix Y coordinate references of the CCD array. The input may also comprise the Z focus location of the eye, and the CLopt and CLth parameters. The output comprises the X and Y coordinate references of the eye at the input Z depth.

FIG. 21 shows the structure of the look up table as in FIGS. 18 to 20. Although a low resolution table is shown, the high resolution table can readily be constructed by a person of ordinary skill in the art based on the teachings described herein. The structure of the table comprises a header and a body comprising columns of the table.

The header may comprise the input and output parameters for the wavelength of the video imaging system. The parameters may comprise the X, Y and Z locations of the imaging system within the eye and the parameters may comprise the corresponding X pixels (Pix X) and Y pixels (Pix Y). The header may comprise coordinate reference locations corresponding to tissue structures of the eye, such as the iris or the limbus, for example. The coordinate reference locations may comprise a location within the eye along the axis of the system at coordinates X=0, Y=0 and Z=8 mm, for example. The corresponding mapped X and Y pixel coordinates for X=5 mm and Y=5 mm can be provided at pixel coordinate locations of approximately 303 pixels, respectively, for example. One of the purposes of the header is to provide a sample of key points within the look up table. These key points may be compared to multiple executions of the model to generate the look up table. These key points can be used as watch points to gain an overview of the performance of the model run and can be used to determine the health or veracity of the look up table.

The body of the look up table may comprise the Pixel X, Pixel Y, Z, CLopt, Clth, input parameters. The output of the look up table may comprise the output X and Y locations for each input record, for example. The corresponding diameter of the spot can be provided at each location in pixels, and a logic flag can be provided for each location. The logic flag may comprise one or more of many logic signals, and may correspond to whether the image of tissue is to be provided at the location, or whether the focus of the treatment beam at the mapped X Pix and Y Pix location is suitable for treatment, for example.

Returning to FIG. 16, in some embodiments, an xy-scan device may be calibrated per the calibration of the video camera with the treatment space. In some embodiments, a xy-scan device of a laser scanning system may be calibrated 104 with the treatment space by first defining control parameters for scanning an electromagnetic radiation beam to a series of XY locations 114. An electromagnetic radiation beam may be scanned per the defined control parameters and the calibrated video camera may be used to capture the scan locations 116. Thereafter, the treatment space may be mapped to the control parameters of the xy-scan device 118.

The movable components of the laser delivery system may comprise a X galvo mirror capable of moving an angular amount Xm, and a Y galvo mirror capable of moving an angular amount $Y_m$. The dimension 153 of machine coordinate reference system 151 may correspond to movement of the X galvo mirror. The dimension 155 of the machine coordinate reference system 151 may correspond to movement of the Y galvo mirror.

Figure 22:
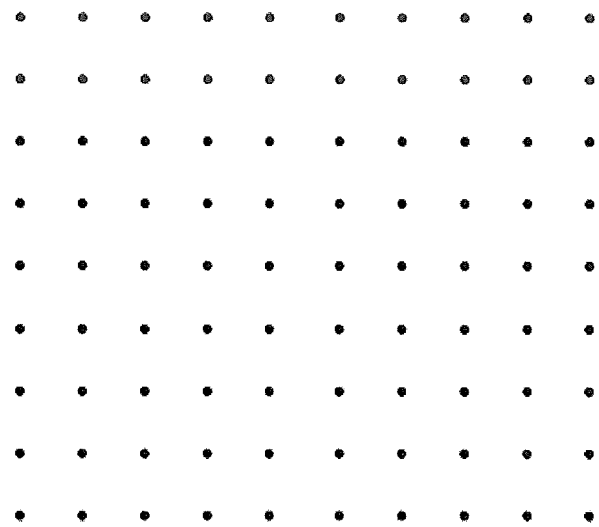
FIG. 22 shows an exemplary scan pattern produced by defined control parameters for calibrating an xy-scan device according to some embodiments of the invention.

In some embodiments, the defined control parameters may be a voltage for actuating the X galvo mirror and the Y galvo mirror. In some embodiments, a voltage space grid may be defined for actuating the X galvo mirror and Y galvo mirror to a plurality of XY locations. In some embodiments, the control parameters may be defined to scan a beam using the xy-scan device to locations of a rectilinear grid or a square lattice, as shown in FIG. 22. For example, the X galvo mirror may be driven by incremental increases in a voltage through a voltage range. Thereafter, the voltage for driving the Y galvo mirror may be increased by an incremental amount and the X galvo mirror may then be scanned through the voltage range using the incremental voltages.

The scanned pattern and/or locations may be captured 116 by the calibrated video camera. In some embodiments, a fluorescent plate may be provided and the beam may be scanned to locations on the fluorescent plate so as to facilitate capture of the scanned pattern by the video camera. The calibrated video camera may then capture electromagnetic radiation reflected from the fluorescent plate in response to the scanned pattern. The pixels of the video camera which capture the reflected electromagnetic radiation may be used to define the physical locations of the scanned XY pattern. The xy-scan device may then be calibrated by mapping the scanned physical XY locations to the defined control parameters using a polynomial fit or a look up table. Accordingly control parameters of the xy-scan device may be correlated to the pixels of the camera and the physical locations. In some embodiments, the voltages for actuating the xy-scan device may be correlated with the physical locations.

In some embodiments, a z-scan device may be calibrated 106 to provide an optimal z-axis laser beam focus at a plurality of depths. In some embodiments, control parameters may be defined for focusing the electromagnetic radiation beam to a series of depth locations 120. Thereafter, the beam may be focused to the series of depths and the scan depths may be captured by the video camera or a confocal detector 122. The treatment space may then be mapped to the control parameters of the z-scan device 124.

Figure 23:
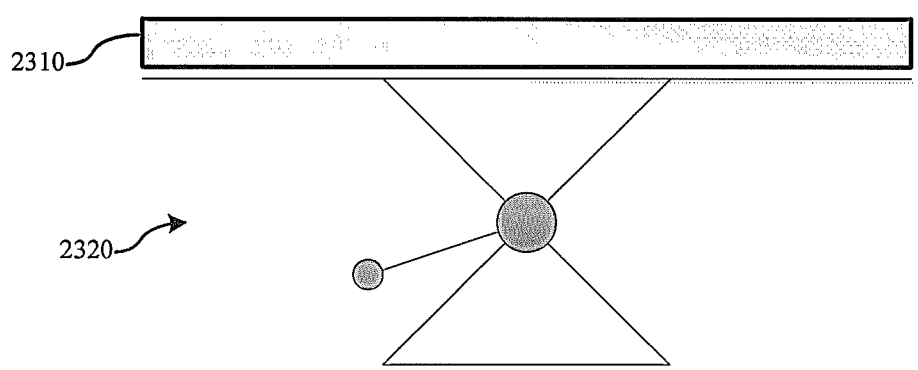
FIG. 23 shows an exemplary jack which may be used for determining a desired depth focus according to embodiments of the invention.

In some embodiments, control parameters such as a voltage for actuating the z-scan device may be defined for focusing the electromagnetic radiation beam to a series of depth locations. The electromagnetic beam may be projected toward an fluorescing plate so as to facilitate identification of the focusing depth. As shown in FIG. 23 the fluorescing plate 2310 may be supported on a jack 2320 and the jack 2320 may set the depth of the fluorescent plate 2310. Optionally, the jack 2320 may be automated and driven to along a range of depths by calibration software or hardware. The jack 2320 may have an adjustable tilt in XY to set the fluorescent plate 2310 perpendicular to the laser beam. The video camera or a confocal detector can be used for determining the focal depth of the electromagnetic radiation beam. In many embodiments, the XY polynomial fit may be independent of Z depth. However, the XY polynomial fit can be a function of Z-depth in some embodiments.

Figure 24A:
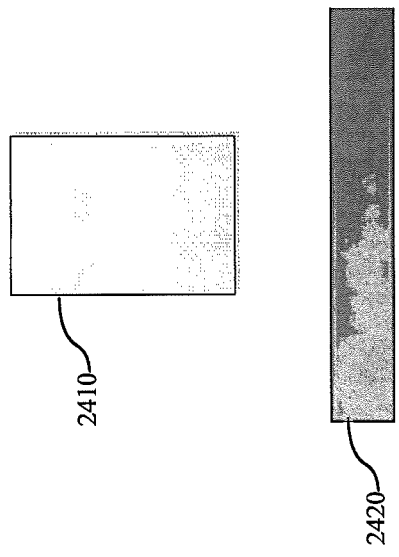
FIGS. 24A-D illustrate an exemplary method and system for calibrating a z-depth of laser system according to some embodiments of the present invention.
Figure 24B:
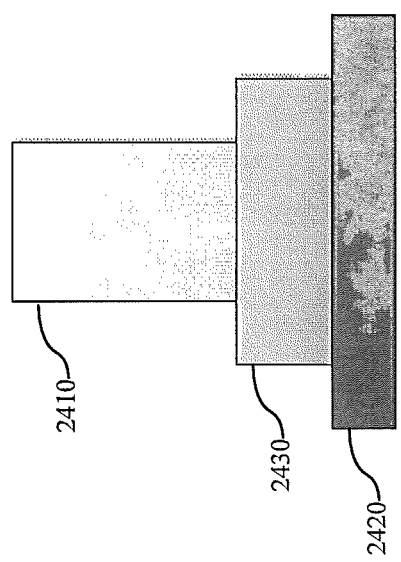
Figure 24C:
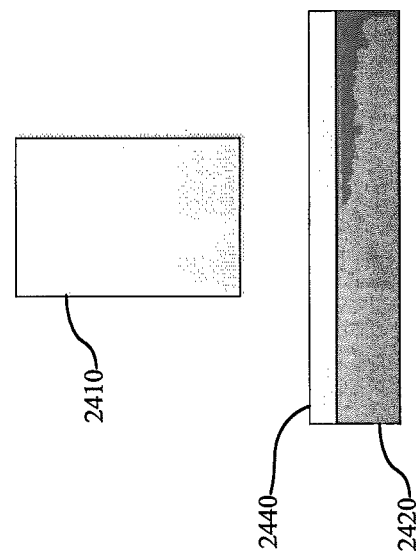
Figure 24D:
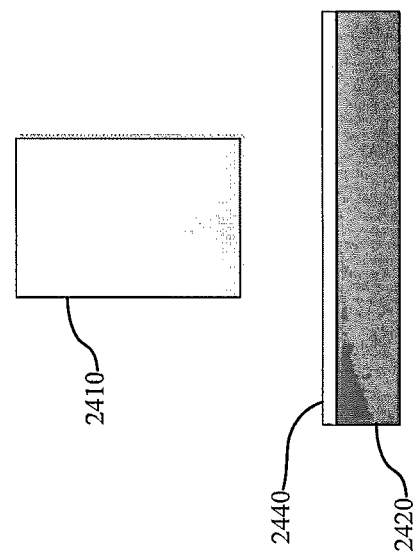

FIG. 24A-24D illustrates another method of calibrating a laser system with a Z-depth. A laser system contact 2410 may be spaced a known distance from a plate 2420. In some embodiments, as shown in FIG. 24A, a disk 2430 with a known depth may be placed between the laser system contact 2410 and the plate 2420. The disk 2430 may have a depth of 4-15 mm in some embodiments. Optionally, disk 2430 may have a depth of 6-10 mm and preferably 8 mm. After positioning the laser system contact 2410 a known distance from the plate 2420, the disk 2430 may be removed as illustrated in FIG. 24B. A fluid 2440, such as water, may then added such that the fluid level increases by incremental amounts as illustrated in FIG. 24C and FIG. 24D. For example, in some embodiments, the fluid level may be increased by one mm increments. In between each fluid level increase, the fluid level may be detected using imaging components of the laser system, such as an OCT imaging system. In some embodiments the fluid level may be increased in three increments of one mm.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

While certain illustrated embodiments of this disclosure have been shown and described in an exemplary form with a certain degree of particularity, those skilled in the art will understand that the embodiments are provided by way of example only, and that various variations can be made without departing from the spirit or scope of the invention. Thus, it is intended that this disclosure cover all modifications, alternative constructions, changes, substitutions, variations, as well as the combinations and arrangements of parts, structures, and steps that come within the spirit and scope of the invention as generally expressed by the following claims and their equivalents.

What is claimed is:

1. A method of calibrating a laser system with a Z-depth, comprising:
   placing a laser system contact at a predetermined distance from a plate;
   placing a fluid on the plate between the plate and the laser system contact;
   incrementally adding the fluid on the plate to increase a fluid level by incremental amounts to a plurality of known fluid levels;
   at each of the plurality of known fluid levels, detecting the fluid level using an imaging system of the laser system; and
   correlating the fluid levels detected by the imaging system with the known fluid levels.

2. The method of claim 1, wherein the step of placing the laser system contact at the predetermined distance from the plate includes:
   placing a disk with a predetermined depth between the laser system contact and the plate, the disk contacting the plate;
   positioning the laser system contact against the disk; and
   removing the disk.

3. The method of claim 2, wherein the disk has a depth of 4-15 mm.

4. The method of claim 2, wherein the disk has a depth of 6-10 mm.

5. The method of claim 1, wherein the fluid level is increased by one mm increments.

6. The method of claim 5, wherein the fluid level is increased in three increments of one mm.

7. The method of claim 1, wherein the fluid is water.

8. The method of claim 1, wherein the imaging system of the laser system is an OCT (optical coherence tomography) imaging system.

* * * * *